United States Patent [19]

Upsher

[11] 4,437,458
[45] Mar. 20, 1984

[54] LARYNGOSCOPE

[76] Inventor: Michael S. Upsher, 2957 Adeline Dr., Burlingame, Calif. 94010

[21] Appl. No.: 324,887

[22] Filed: Nov. 25, 1981

[30] Foreign Application Priority Data

Nov. 27, 1980 [EP] European Pat. Off. ....... 80 107427.9

[51] Int. Cl.³ .............................................. A61B 1/06
[52] U.S. Cl. .................................................... 128/11
[58] Field of Search ..................... 128/6–11, 128/13, 16, 18, 22, 23

[56] References Cited

U.S. PATENT DOCUMENTS

| | | | |
|---|---|---|---|
| 1,339,711 | 3/1920 | Park | 128/16 |
| 2,354,471 | 7/1944 | Macintosh | 128/10 |
| 3,384,076 | 5/1968 | Spedman | 128/9 |
| 4,273,112 | 1/1981 | Heine et al. | 128/11 |
| 4,306,547 | 12/1981 | Lowell | 128/11 |

FOREIGN PATENT DOCUMENTS 2361855  3/1978  France ................................. 128/11

Primary Examiner—Edward M. Coven
Assistant Examiner—Max F. Hindenburg
Attorney, Agent, or Firm—Flehr, Hohbach, Test, Albritton & Herbert

[57] ABSTRACT

An improved laryngoscope having a blade which is curved and tubular and has an improved light means for illuminating the forward end of the blade. In a number of embodiments of the laryngoscope, a light source is mounted in the upper end of the handle of the laryngoscope so the handle can be used with a conventional laryngoscope blade or a non-conventional laryngoscope blade. In one embodiment, the light source is carried by an adapter removably mounted on the handle near the location where the handle and blade are interconnected.

13 Claims, 55 Drawing Figures

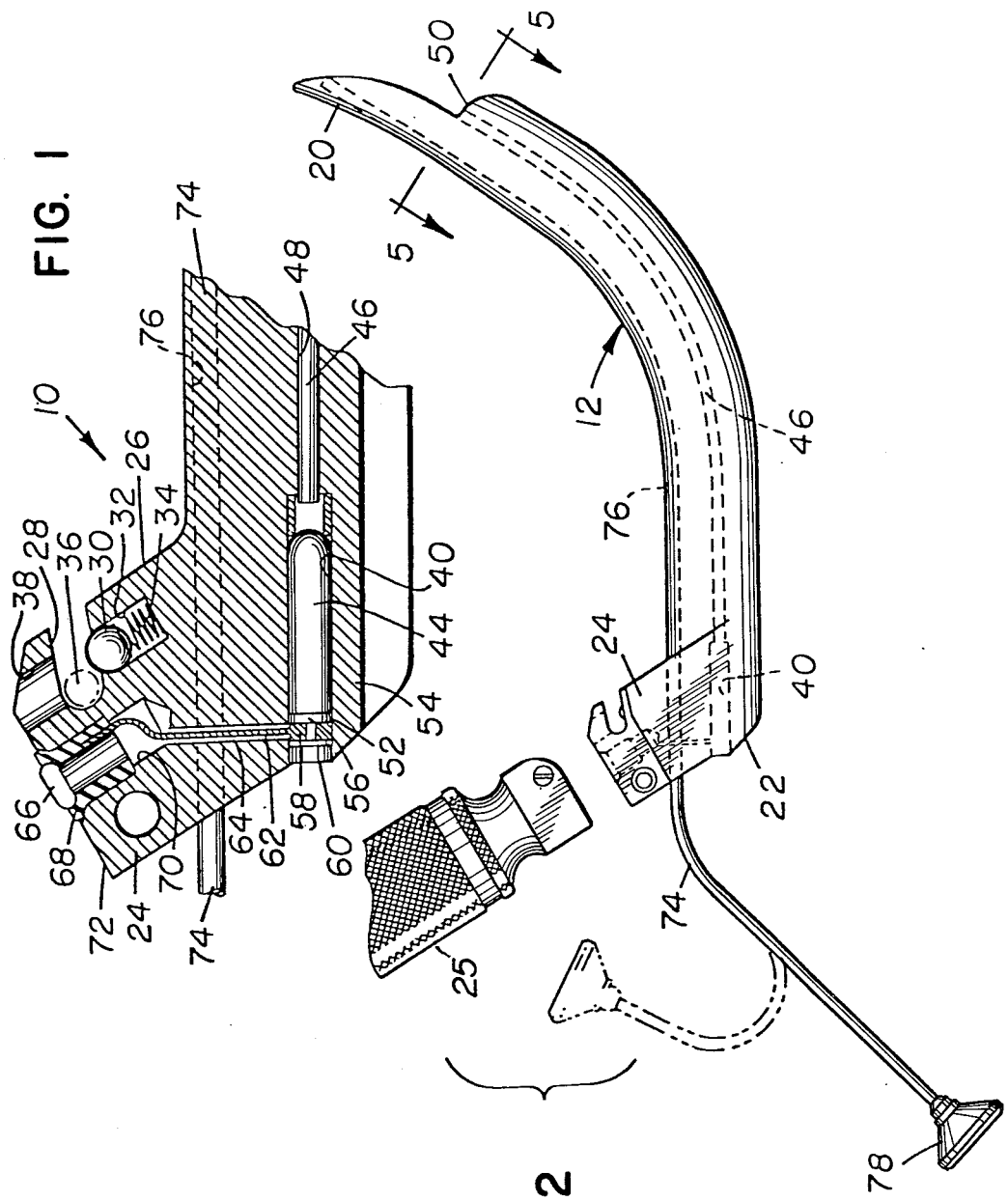

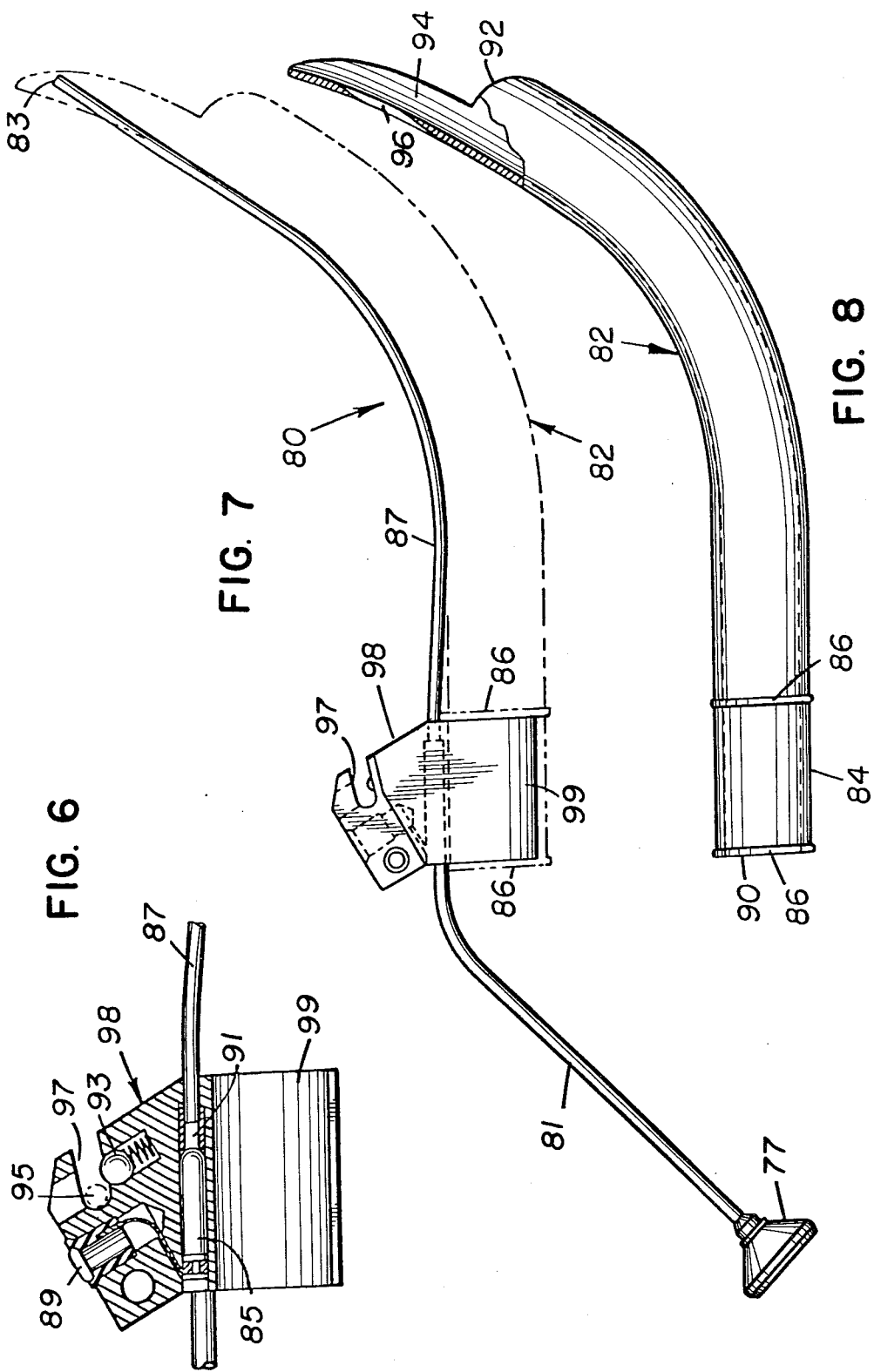

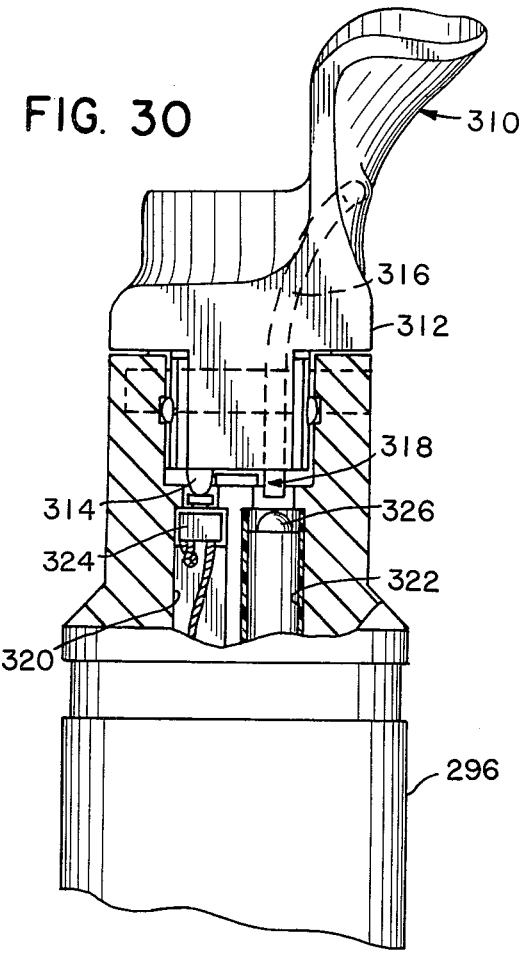
FIG. 30
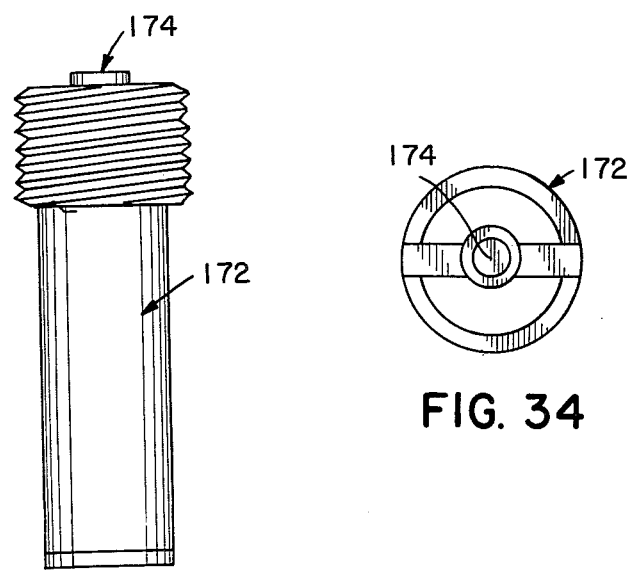
FIG. 33
FIG. 34

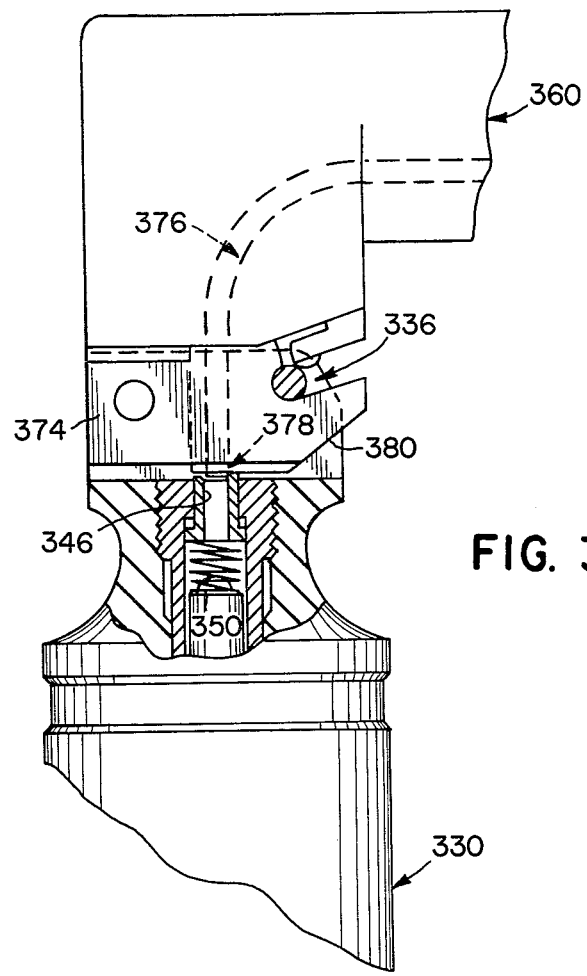
FIG. 35
FIG. 36
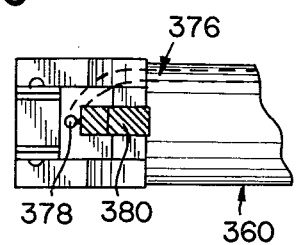
FIG. 37
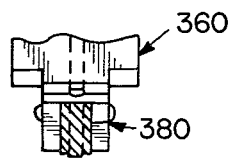

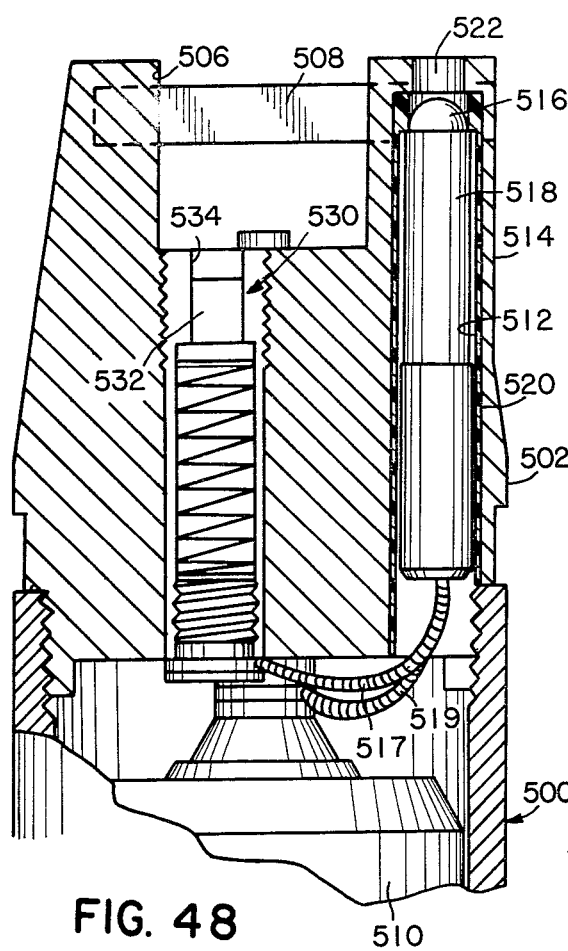
FIG. 48
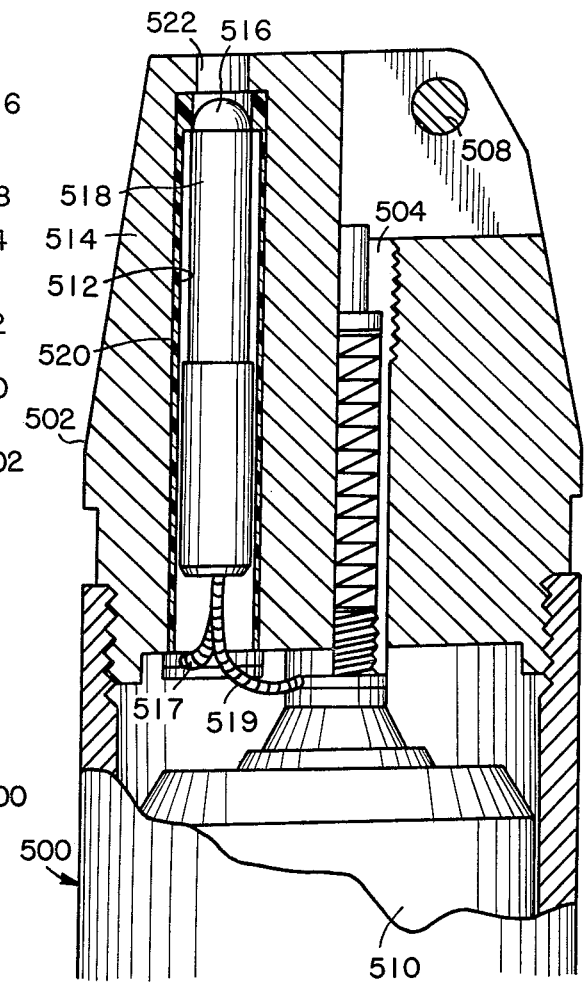
FIG. 49
FIG. 50
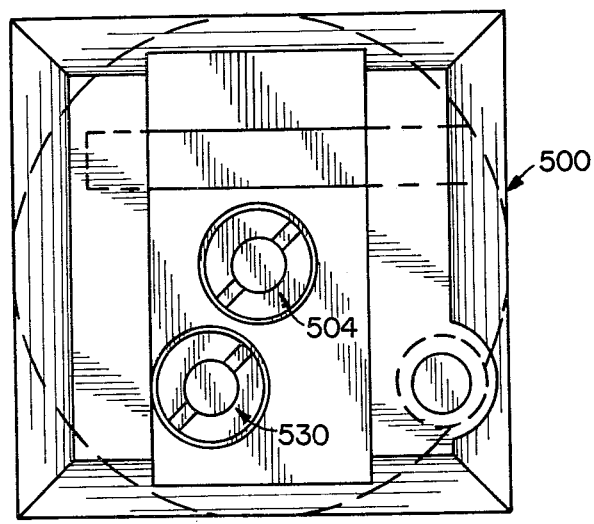

LARYNGOSCOPE

In using conventional laryngoscopes, it is only by trial and error that the blade of the laryngoscope can be inserted into the pharynx in such a manner to elevate the epiglottis so that an endotracheal tube can be manually moved into the throat and into the larynx. This is because the larynx cannot always be directly and completely viewed during insertion of the blade. Usually, the laryngoscope is held in one hand as the endotracheal tube is held in the other hand because the laryngoscope has no means for both removably holding and guiding the endotracheal tube. This is an awkward situation because the user of the laryngoscope must be able to probe the pharynx without actually seeing the epiglottis in an attempt to elevate it, yet the user must be ready to insert the tube as soon as the epiglottis is elevated. Most importantly, the line of sight from the eye of the anesthesiologist to the epiglottis and the larynx must be straight using direct vision; whereas, the endotracheal tube must frequently be passed in a curved manner to conform with the normal anatomical pharyngeal curvature. The anesthesiologist, in these cases, is therefore asked to straighten out the normal physiological curve of the pharynx. This may result in damage to the patient's teeth and "soft parts." Thus, considerable time and effort is expended in elevating the epiglottis and then inserting the tube, all of which must be done while causing only a minimal amount of discomfort to the patient.

The insertion of a conventional laryngoscope in the throat is a very tedious process in many cases and, in some cases, injury is caused to the patient by virtue of the movements of the laryngoscope blade within the narrow confines of the anatomical limitations of the patient. No satisfactory laryngoscope has been heretofore provided for effectively guiding the endotracheal tube into the throat while providing for the direct and indirect viewing of the throat during the insertion of the blade to elevate the epiglottis.

Representative laryngoscopes are disclosed in the following U.S. Pat. Nos. 2,646,036, 3,986,854 and 4,086,919. An endoscope which is related to a laryngoscope is disclosed in U.S. Pat. No. 3,896,793. The laryngoscopes of these references do not provide for the guiding of an endotracheal tube while permitting direct and indirect viewing of the throat during insertion of the blade of the laryngoscope. Moreover, there is no teaching or suggestion in these references that the blade can be shaped to fit different anatomical throat configurations of various patients nor do the references suggest the need for improvement in laryngoscope blades.

Another problem associated with conventional laryngoscopes is that the blade has a light bulb serving as a light source and the light bulb is located near the outer end of the blade. This light bulb is in a cylindrical part which projects laterally and outwardly of the outer surface of the blade, an undesirable feature. The light bulb is electrically connected by a conductor wire and by the metallic base of the blade to a battery in the handle of the laryngoscope when the handle is coupled to the base of the blade, the handle being separable from the base of the blade. The conductor wire sometimes becomes detached from the light bulb for one reason or another and this requires repair of the connection between the wire and the light bulb before the laryngoscope can be properly used again.

The wire is usually carried in a rigid conduit secured to the outer side of the blade and extending from the base along the blade to the outer end of the blade. This conduit further adds to the maximum transverse dimension of the blade. Also, the presence of moisture, such as saliva, in and around the connection between the conductor wire and the light bulb has an adverse effect on the operation of the bulb.

The present invention satisfies a need for an improvement laryngoscope which eliminates the trial and error techniques used in the past with conventional laryngoscopes for elevating the epiglottis. To this end, the laryngoscope of the present invention has a tubular blade provided with a passage for guiding an endotracheal tube into the larynx and trachea so that the insertion of the blade in the throat to elevate the epiglottis can be immediately followed by the passage of the tube through the tube-guiding part of the blade following which the blade can be removed, leaving the tube in place in the larynx and trachea. The blade has a slot on its back margin to permit direct viewing of the pharynx during initial insertion of the blade. For an intubating laryngoscope, this slot extends throughout the length of the blade and serves the additional purpose of allowing the removal of the laryngoscope from the pharynx while leaving the endotracheal tube in place. The slot is narrow enough to hold the tube in the blade but is wide enough to allow the tube to be separated from the blade when the tube yeilds so as to become elliptical in shape sufficiently to squeeze or pass through the slot. If the laryngoscope is of the operating type, the slot does not extend throughout the length of the blade but extends only a short distance from the outer end of the blade.

Other improvements of the laryngoscope of the present invention include the fact that the viewing slot, instead of being on the back margin of the blade, can be at any location within an arc 90° on each side of the back margin. This feature provides greater length of insertion of the blade before direct viewing is blocked due to the curvature of the blade. Also, the blade can be made of a suitable material which allows the blade to be normally rigid but capable of being flexed or shaped to fit the anatomical throat configurations of different patients.

The present invention satisfies another need by providing a laryngoscope having a blade with an improved base for connection to a conventional laryngoscope handle wherein the base has a bore formed therein for housing a light bulb which, in association with a light guide extending from the bore to the outer end of the blade, serves as the light source for illuminating the region in advance of the outer end of the blade. In this way, the bulb will not present a projection at the outer end of the blade as in conventional laryngoscopes and the light guide itself conveys the light from the bulb in the base to the outer end of the blade. Thus, the outer end face of the light guide becomes the light source with respect to the region in advance of the blade.

Electrical connection between the battery and bulb is made in any suitable manner. For instance, the base can be provided with a terminal connected by a wire to the central contact of the bulb, and this terminal is placed in electrical contact with the central terminal of the battery in the handle when the handle is coupled to the base of the blade. The base and handle are of metallic material to form the other conductor between the battery and the bulb when the handle is coupled to the base.

In one embodiment of the present invention, the blade is curved and the blade and base are integral with each other. The blade has a tubular configuration with a slot to guide an endotracheal tube into the trachea of a patient, the slot being provided to permit separation of the blade from the endotracheal tube after the tube has been inserted into the trachea.

In other embodiments, the blade and base can be separable from each other. This permits the blade to be disposable and made sufficiently inexpensive to permit it to be thrown away after a single use. To this end, the base has a tubular connector part which releasably receives one end of the blade, the latter being of a yieldable material so that the end of the blade can be snap-fitted into place into the connector part of the base. In the alternative the connector part of the base can be yieldable and the end of the blade can be rigid. The disposable blade also has a tubular configuration and a slot for guiding an endotracheal tube into place and for permitting separation of the blade from the endotracheal tube.

With the disposable tube, a light guide is carried by the base and extends outwardly from the base and along the blade and removably through an opening near the outer end of the blade. This allows the blade to become separated from the light guide as well as the base yet the light guide can transmit light along the blade and to the outer end of the blade. A second light guide for viewing the illuminated area in advance of the blade can be provided as a separate element or can be formed with the first-mentioned light guide as a single unit.

Other ways of mounting the light source can be provided. For instance, the light source can be in the laryngoscope handle or an adapter removably mounted on the handle. Also, a handle with a light therein can be provided which can be used with a conventional laryngoscope blade or with a non-conventional disposable or non-disposable blade.

An important object of this invention is to provide an improved laryngoscope which permits both direct and indirect viewing of the pharynx and larynx as the blade of the laryngoscope is inserted into the pharynx yet the blade has means for guiding an endotracheal tube in the place in the throat to thereby eliminate a trial and error method of elevating the epiglottis and guiding the endotracheal tube into position.

Another object of the present invention is to provide a laryngoscope of the type described which permits shaping of the blade to accommodate different throat configurations of various patients without destroying the capability of the blade to guide an endotracheal tube into the larynx past the epiglottis after the latter has been elevated by the blade.

A further important object of this invention is to provide an improved laryngoscope in which the light source is carried in the base of the blade and the light from the light source is transmitted to the outer end of the blade by a light guide to provide increased reliability for the light source while permitting the use of the handle of a conventional laryngoscope with the base and blade.

Another object of the present invention is to provide an improved laryngoscope having a light source of the type described wherein the blade can either be integral with the base or removably mounted on the base to permit the blade to be thrown away after a single use.

Another object of this invention is to provide an improved laryngoscope handle having a large light bulb therein which can be the light source for a non-conventional laryngoscope blade with a fiber optic light guide, yet the handle can also be used with a conventional laryngoscope blade and the blade used with the handle can be disposable or non-disposable.

IN THE DRAWINGS

FIG. 1 is a fragmentary, cross-sectional view of a portion of an improved laryngoscope blade of the present invention, showing the light source carried by the base integral with the blade;

FIG. 2 is a side elevational view of the tubular blade of this invention showing fiber optic light and visual guides in dashed lines extending along the length of the blade;

FIG. 6 is a view similar to FIG. 1 but showing the base and attachment means for a semi-rigid, disposable laryngoscope blade separable from the base;

FIG. 7 is a view similar to FIG. 2 but showing the disposable blade removed from the base but the blade being shown in dashed lines;

FIG. 8 is a side elevational view of the blade for releasable attachment to the base of FIG. 7;

FIG. 30 is a side elevational view, partly in section, of a handle having a bulb mounted in the upper end thereof for use with a laryngoscope blade;

FIG. 33 is a side elevational view of the cartridge of FIG. 32;

FIG. 34 is a top plan view of cartridge of FIG. 33;

FIG. 35 is another type of blade with a handle with a light bulb in a central cartridge;

FIG. 36 is a bottom plan view of a portion of the blade for use with the handle of FIG. 35;

FIG. 37 is a front elevational view of the blade of FIG. 36;

FIG. 48 is a view similar to FIG. 13 but showing a light bulb in a side portion of the handle;

FIG. 49 is another view of the handle of FIG. 48;

FIG. 50 is a top plan view of the handle of FIG. 48;

Figure 3:
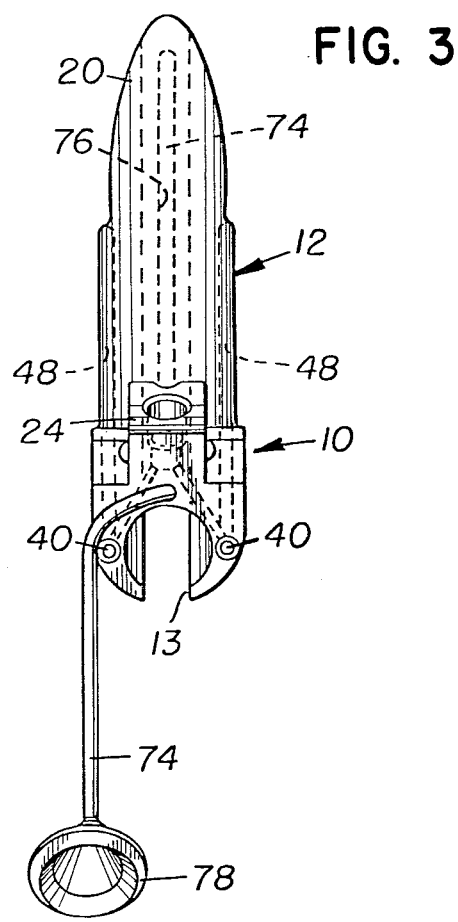
FIG. 3 is a perspective view of the laryngoscope blade of FIG. 2, looking in the direction of the end of the blade adjacent to the base thereof.

A first embodiment of the laryngoscope of the present inventions is broadly denoted by the numeral 10 and is shown in FIGS. 1–4. Unit 10 includes a tubular laryngoscope blade 12 which is curved in the manner shown in FIG. 2 and provided with slot 13 along its length in the manner shown in FIG. 5 to present a top portion 14 and a pair of sides 16 and 18. The blade is tubular throughout its entire length except for an end tip 20 which serves to elevate the epiglottis of a patient when the blade is inserted into the pharynx and larynx of the patient. The tubular and slotted nature of the blade permits an endotracheal tube (not shown) to be inserted in an open end (FIG. 2) 22 of blade 12 and to be guided along the blade so that the tube can emerge near tip 20 after the blade has been inserted into the throat of a patient. This allows the tube to enter the patient's trachea for intubation as is well known. The tube is curved to permit it to follow the conformation of the throat and to facillitate insertion of blade 12 into the throat prior to intubation. The blade could also be of a material which is normally rigid but can be flexed or shaped to fit different throat configurations. Slot 13 permits separation of the blade from the endotracheal tube when the latter is in the trachea.

Blade 12 has a base 24 adjacent to end 22 thereof, the base adapted to be coupled in a well-known manner to a conventional laryngoscope handle 25 (FIG. 2) containing a battery (not shown) for energizing a light source hereinafter described. Base 24 has a surface 26 provided with a groove 28 therein for receiving the cross-bar 36 on the handle. A ball detent 30 in a bore 32 in the base is spring biased into grove 28 by a spring 34 so that the ball releasably holds bar 36 in place in the dashed line position of FIG. 1 to releasably connect the handle to the blade. A bore 38 is formed in base 24 to facilitate the drilling of bore 32.

Figure 5:
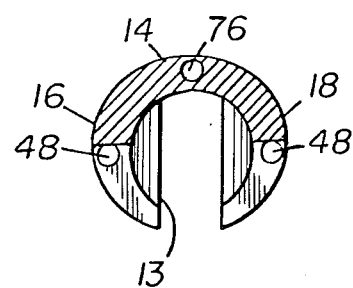
FIG. 5 is a cross-sectional view taken along line 5—5 of FIG. 2.
Figure 4:
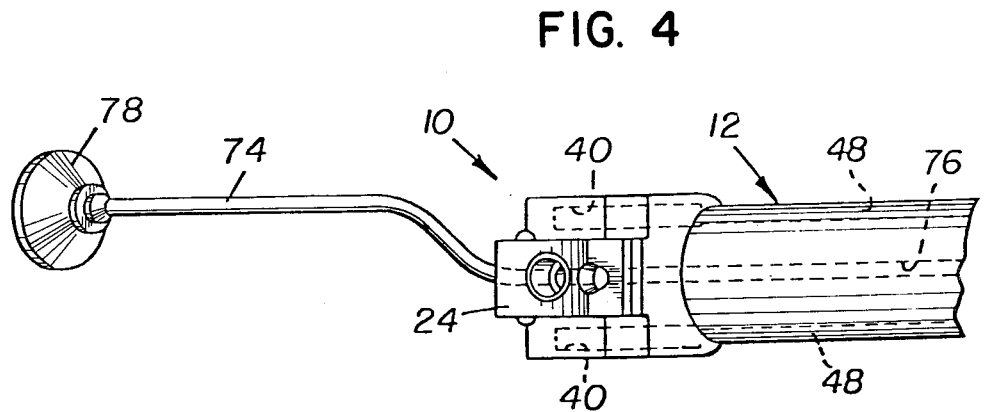
FIG. 4 is a fragmentary, perspective view of the blade looking downwardly from above the blade shown in FIG. 2.

Blade 12 has a pair of bores 40 (FIGS. 1 through 4) at the opposed sides thereof which removably receive respective light bulbs 44, only one of which is shown in FIG. 1. The light bulbs define light sources which are energized by the battery in the handle when the handle is connected to blade 12, and the light from the light source is directed out of bores 40 through fiber optic light guides 46 which extend into and through bores 48 extending along and through the opposed sides 16 and 18 of blade 12 as is shown in FIGS. 4 and 5. The light guides terminate at end edges 50 (FIG. 2) of blade 12, and the end faces of light guides 46 define the light sources which project light forwardly of the outer end of the blade and longitudinally of tip 20 to illuminate a patient's throat area in advance of the blade when the blade is being inserted into the throat. While a pair of light sources or light bulbs 44 have been shown for purposes of illustration, it is clear that only one light bulb could be deemed necessary. The fact that light sources are in the base of the blade rather than mounted externally of the blade near edges 50 permits a compact assembly of light source and blade and eliminates electrical contact problems as well as heat that is generated in the vicinity of edges 50 when the light bulb or light source is adjacent to such edges.

Means is provided to electrically connected each light bulb 44 to the battery in the handle when the handle is coupled with the blade. For instance, each light bulb 44 is provided with a bulb jacket 52 which makes electrical contact with the adjacent metallic portion 54 of base 24, and the bulb has a center terminal 56 engaged by a contact ring 58 electrically insulated from base portion 54 and held in place by an electrically threaded access cap 60 threaded into bore 40. A conductor wire 62 in electrical contact with contact ring 58 is directed through a respective bore 64 and makes electrical contact with an electrical terminal 66 press-fitted by means of a rubber grommet 68 in a second larger bore 70 extending into the end face 72 of base 24. Terminal 66 is common to the wires 62 of both bulbs 44.

When base 24 is releasably coupled to the handle with cross-bar 36 in the dashed line position of FIG. 1, terminal 66 makes electrical contact with the corresponding center terminal (not shown) of the battery in the handle. Moreover, bar 36, which is metallic, makes electrical contact with the bottom terminal of the battery and with base 24 so that the electrical circuit through the battery and the bulbs is completed, whereupon the bulbs are energized and the light from the bulbs passes through respective light guides 46 to their end faces near edges 50.

A fiber optic visual guide 74 extends through a bore 76 along the top of blade 12, and this visual guide extends through base 24 and outwardly therefrom. Visual guide 74 has an eyepiece 78 which permits viewing of the illuminated area in advance of the blade. Moreover, the part of light guide 74 extending outwardly from base 24 is flexible so that eyepiece 78 can be placed at various positions relative to the blade for the convenience of the user.

In use, blade 12 is releasably coupled to the handle and this causes the light bulbs to be energized immediately. Then, either while sighting through eyepiece 78 or viewing the pharynx directly through the slot in the blade, the user inserts the blade into the throat of the patient, during which time the throat area is illuminated by the light emanating from light guides 46 and the reflected light can be viewed through directly or through visual guide 74. When the blade is properly inserted in the pharynx and larynx, the endotracheal tube is guided through the tubular portion of blade 12 and into the trachea of the patient, following which the blade can then be separated from the endotracheal tube by causing the tube to pass through slot 13 of the blade while the blade is removed from the throat as the endotracheal tube remains.

FIGS. 6-8 show another embodiment of the laryngoscope blade unit of this invention in which the blade is separable from the base so that the blade can be disposed of after a single use. However, the blade need not be disposable. It can be of metallic material and be washable and capable of being sterilized.

The improved embodiment of FIGS. 6-8 includes a laryngoscope 80 having a blade 82 of substantially the same shape and cross-section as blade 12 of unit 10 except that blade 82 has an end portion 84 provided with a pair of spaced flanges 86 which partially surround blade 82 and have ends which terminate at the slot (not shown) of the blade, the slot extending throughout a major portion of the blade from end 90 thereof to the opposite end margin 92 near a tip 94 provided with an opening 96.

A base 98 is used with blade 82, and base 98 has a cylindrical, slotted connector section 99 which removably receives end portion 84 of blade 82. FIG. 7 shows the blade in dashed lines in coupled relationship with section 99 with flanges 86 on the end portion 84 of the blade being adjacent to opposed ends of section 99 so as to provide a snug fit for end portion 84 and to prevent axial movement of blade 82 relative to section 99.

Base 98 is of substantially the same construction as base 24 of unit 10 (FIG. 1) except that base 98 is not integral with a blade as is base 24. This is shown in more detail in FIG. 6 wherein base 98 has a groove 97 for receiving the cross bar 95 (corresponding to cross bar in FIG. 1) of a handle (not shown) containing a battery, the handle being conventional in construction. A ball detent 93 is spring biased partially across groove 97 to hold bar 95 in place.

Base 98 further has a central bore 91 therethrough for containing a light bulb 85 which serves as a light source for blade unit 80. The bulb is electrically connected to a terminal 89 and to base 98 itself in the manner described above with respect to the electrical connection of bulbs 44 to a battery in a conventional handle. Thus, a description of the electrical connection of the FIG. 1 embodiment suffices for the FIG. 6 embodiment.

A fiber optic light guide 87 extends into a continuation of bore 91 to receive light from bulb 85. Light guide 87 is adapted to be removably inserted at its outer end 83 into hole 96 of blade 82 so that the outer end 83 of the light guide will terminate near tip 94 to direct light forwardly of tip 94 to illuminate the region in advance of the tip.

A fiber optic visual guide 81 has an eyepiece 77 which extends outwardly from base 98 in the opposite direction from light guide 87. Visual guide 81 has an intermediate part which merges smoothly with light guide 87 and the fibers of visual guide 81 are also embedded in light guide 87 and terminate at end face 83. Commercial fiber optic bundles are available to serve this particular purpose. Thus, light travels from light bulb 85 along light guide 87 to end face 83, whereupon reflected light from an object in advance of end face 83 is received by the fiber optic end face of visual guide 81 and the reflected light travels through visual guide 81 and eyepiece 77. In this way, only a single fiber optics guide is associated with tube 82 to minimize the structure projecting from the outer surface of the blade. While light guide 87 is shown on the back portion of blade 82, it could be at either side as well.

Laryngoscope blade unit 80 is placed in use by first inserting the outer end of light guide 87 through hole 96 of blade 82. Then, end portion 84 of blade 82 is snap-fitted into section 99 of base 98. For this purpose, end portion 84 can be of a semi-rigid or yieldable material, such as a suitable plastic, i.e., polyethelyne or the like. The entire blade, including end portion 84, can be made of this yieldable material. In the alternative, end portion 84 can be of yieldable material and bonded to the remainder of the blade which can be of another material. Instead of a yieldable end portion 84, the latter can be rigid and section 99 on the base 98 can be of a yieldable material.

When base 98 is releasably coupled to the handle, electrical contact is made between the battery and bulb 85, causing the bulb to be activated which illuminates the area in advance of end face 83 of light guide 87. Then, the blade can be inserted into the patient's throat in the manner described above with respect to blade unit 10. Thus, the reflected light, viewed through eyepiece 77, will assist the user of unit 80 in the insertion of the blade into the throat. When the blade is properly inserted, an endotracheal tube is then directed into the open outer end of blade 82 and guided by the blade into and along the blade and eventually into the trachea of the patient. Then, the endotracheal tube and blade 82 can be separated from each other by virtue of the slot (not shown) in the blade so that blade 82 can be removed from the throat of the patient leaving the endotracheal tube in place.

While light bulb 85 is shown centrally of base 98 as indicated in FIG. 6, it is possible that the bulb can be at one side or the other of the base and still be operable. Preferably it is at the center so that light guide 87 can be centrally located relative to blade 82.

Figure 9:
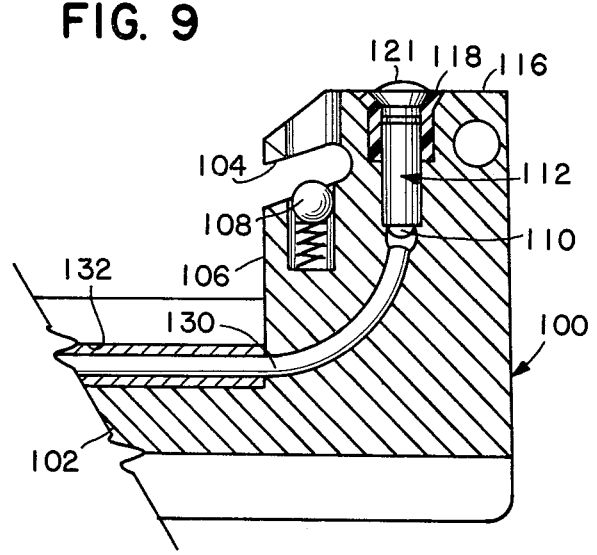
FIG. 9 is a view similar to FIG. 1 but showing another base for a laryngoscope blade.

FIG. 9 is a view similar to FIG. 1 but showing another embodiment 100 of a base for a laryngoscope blade 102. A slot 104 for receiving the crossbar on a standard handle extends into face 106 of base 100. A ball detent 108 is spring biased into slot 104 for the same reasons as ball 30 of the base of FIG. 1.

Figure 10:
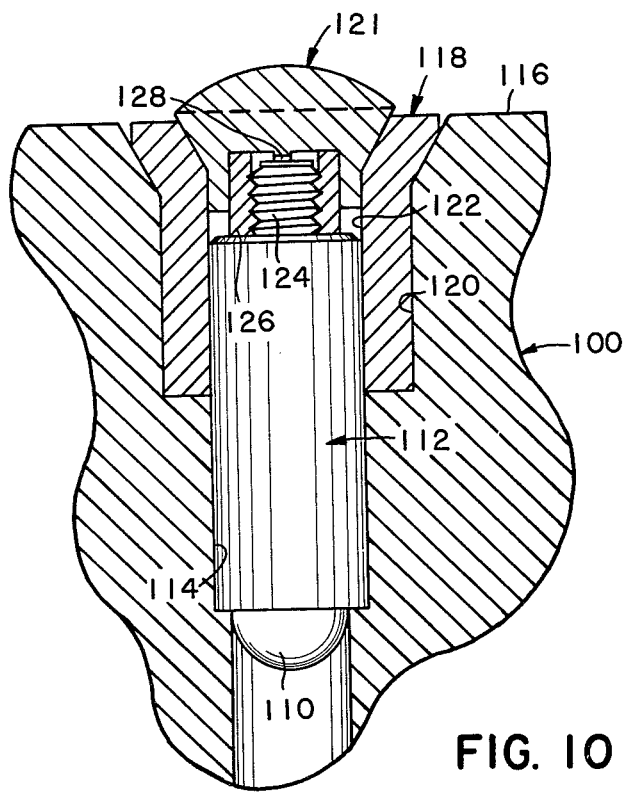
FIG. 10 is an enlarged, fragmentary cross-sectional view of the bulb in the base of FIG. 9.

A light bulb 110 is received in a cylindrical housing 112 (FIG. 10) in a passage 114 extending into the base from end face 116 thereof. An insulator 118 is press fitted into a second passage 120 and holds housing 112 in place in passage 114. An electrical contact 121 is press fitted into the central bore 122 of insulator 118 and makes electrical contact through a threaded projection 124 extending into a second tubular insulator 126 between the annular extension 128 of contact 121 and threaded end 124. Contact 121 is to be coupled electrically to the corresponding electrical contact on a standard handle when the handle is coupled to base 100 in the usual fashion. This causes bulb 110 to be energized to direct light through a fiber optic bundle 130 (FIG. 9) which extends through base 100 and along a passage 132 in blade 102.

Figure 11:
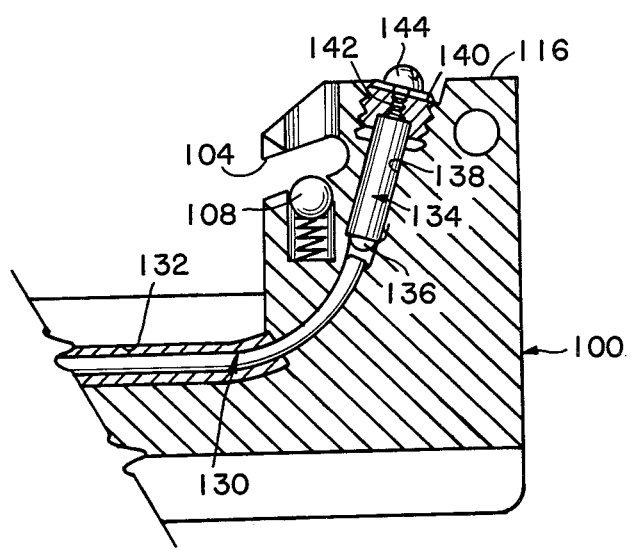
FIGS. 11 and 12 are views similar to FIG. 9 but showing additional ways of mounting the bulb in the base.
Figure 12:
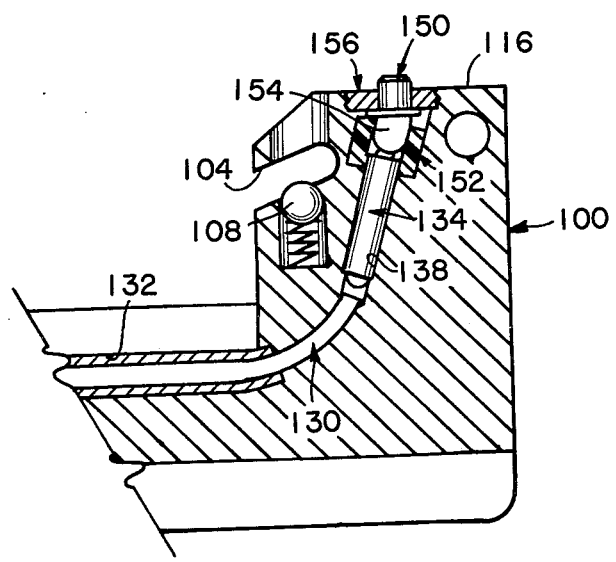

Preferred embodiments of blade base 100 are shown in FIGS. 11 and 12 in which another type of housing 134 having a bulb 136 extends in an inclined passage 138 in base 100. In FIG. 11, an insulator 140 surrounds base screw 142 making contact with the center top pin of bulb 136 and screw 142 has a head 144 defining the end contact for the bulb. This head projects outwardly from end face 116 of base 100. The other electrical connection is through the base of housing 134 and base 100.

FIG. 12 shows that housing 134 can have an electrical contact 150 which project straight out from end face 116 rather than at an angle as shown in FIG. 11. A spacing grommet 152 receives one end 154 of contact 150, the opposite end of the contact being at an angle with relative to end 154 as shown in FIG. 12. Contact 150 passes through an insulator 156 threaded into the end of face 116 of base 100. In both embodiments of base 100 as shown in FIGS. 11 and 12, fiber optics bundle 130 mates easily with passage 138.

Figure 13:
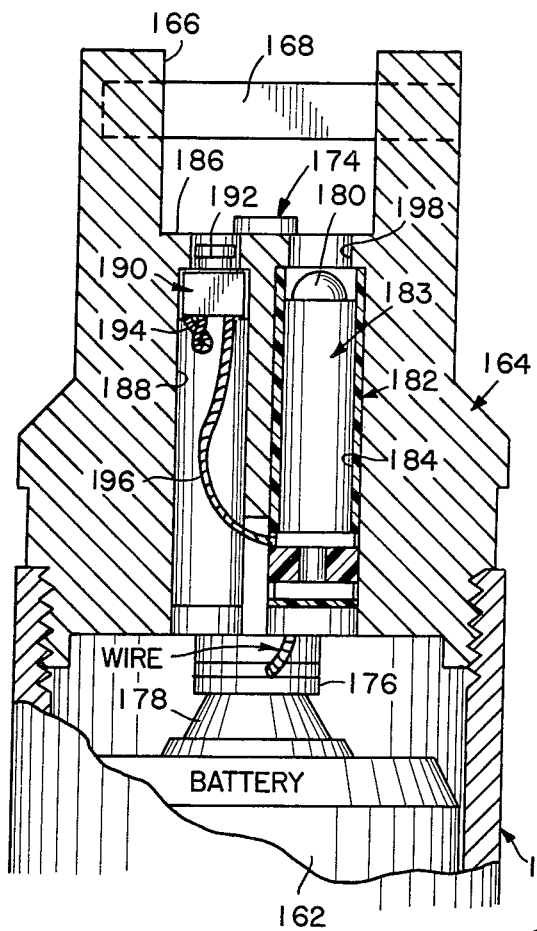
FIG. 13 is an enlarged, fragmentary cross-sectional view of a laryngoscope handle having a bulb mounted therein for a standard laryngoscope blade or a blade having a fiberoptics bundle for transmitting light to the outer end of the blade from the light bulb in the handle.
Figure 15:
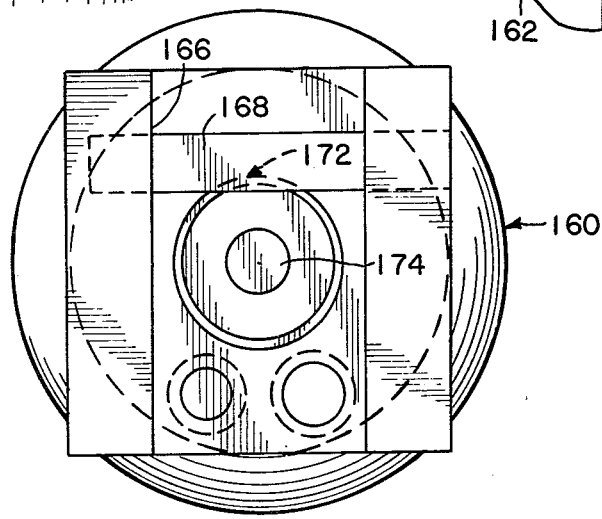
FIG. 15 is a top plan view of the handle of FIG. 13.

FIG. 13 shows a laryngoscope handle 160 containing a battery 162 and provided with a threaded end member 164 having a slot 166 at the upper end thereof. A crossbar 168 at end 166 is adapted to be inserted into a usual slot, such as slot 104 of base 100 (FIG. 9) for connecting the base to the handle. However, in the case of handle 160, member 164 has a space 170 for a cartridge normally found in a standard laryngoscope handle, such as a standard cartridge 172 of the type shown in FIG. 15. The cartridge has a contact 174 at its upper end which, through a spring (not shown) inside the housing of the cartridge, makes electrical connection with an end contact 176 which, as shown in FIG. 13, engages the end terminal 178 of battery 162.

Member 164 has a bulb 180 in a cylindrical housing 183 and an insulator 182 disposed within a passage 184 extending inwardly from the end face 186 of member 164. A second passage 188 parallel with passage 184, contains a microswitch 190 having a pushbutton actuator 192 recessed inwardly from end face 186. Also, bulb 180 is spaced inwardly from end face 186. Wires 194 and 196 make electrical connection between battery 162, a light bulb 180 and microswitch 190 when the microswitch is actuated as its actuator 192 is forced inwardly.

Handle 160 is to be used with a conventional laryngoscope blade or a non-conventional blade of the type having a base provided with a fiber optics bundle which is insertable within the opening 198 forming a part of passage 184. The non-conventional blade base also has a projection for insertion into the upper open space above actuator 192 of microswitch 190 so that when the projection is forced into this opening, actuator 192 is depressed it closes switch 190 to connect battery 162 and light bulb 180. Then, light will be transmitted through the fiber optics bundle to the outer end of the laryngoscope blade. If a conventional blade is used, voltage from the battery 162 is supplied to the light bulb at the outer end of the blade through standard cartridge 172 in the usual manner.

Figure 18:
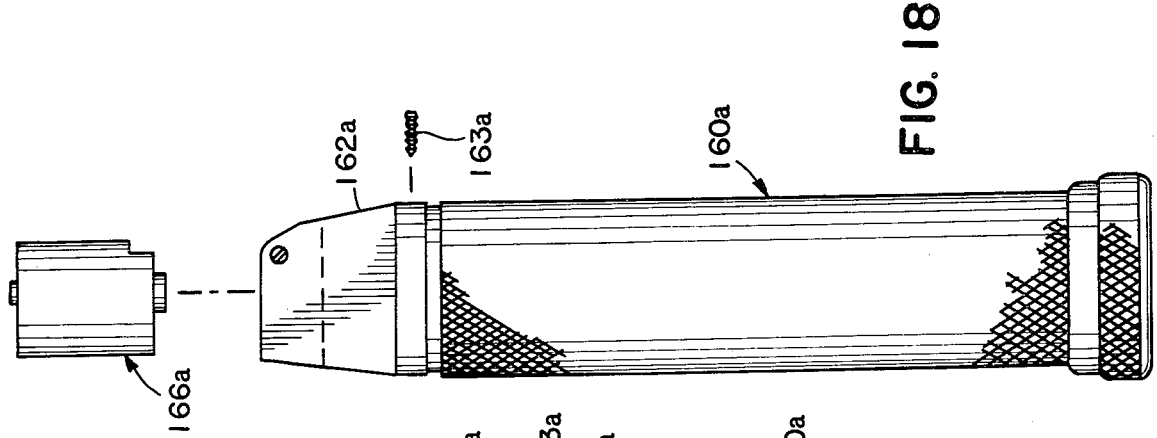
FIG. 18 is an exploded view of the handle showing the cartridge for insertion thereinto.
Figure 17:
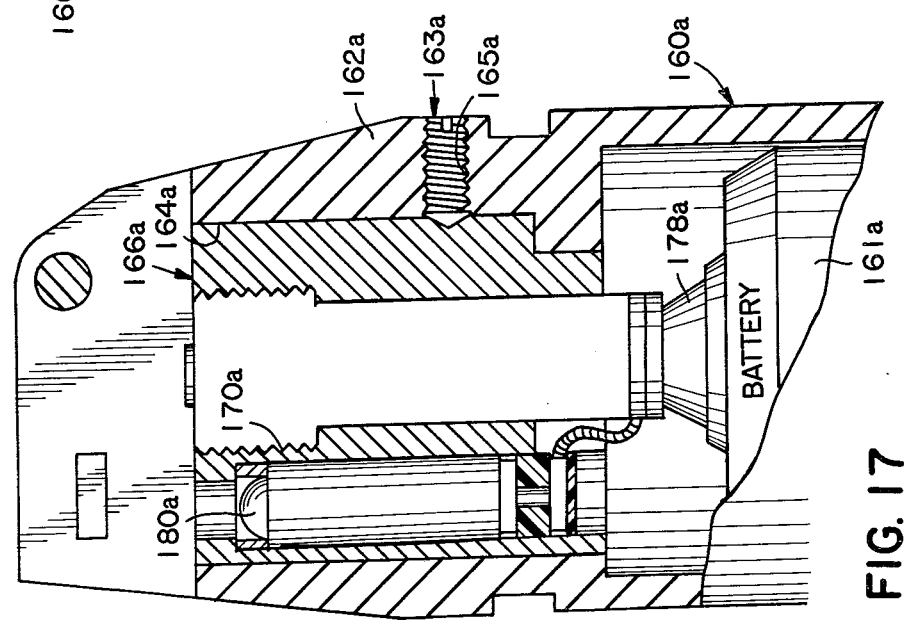
FIG. 17 is a view of the cartridge of FIG. 16 but rotated through an angle of 90°.
Figure 16:
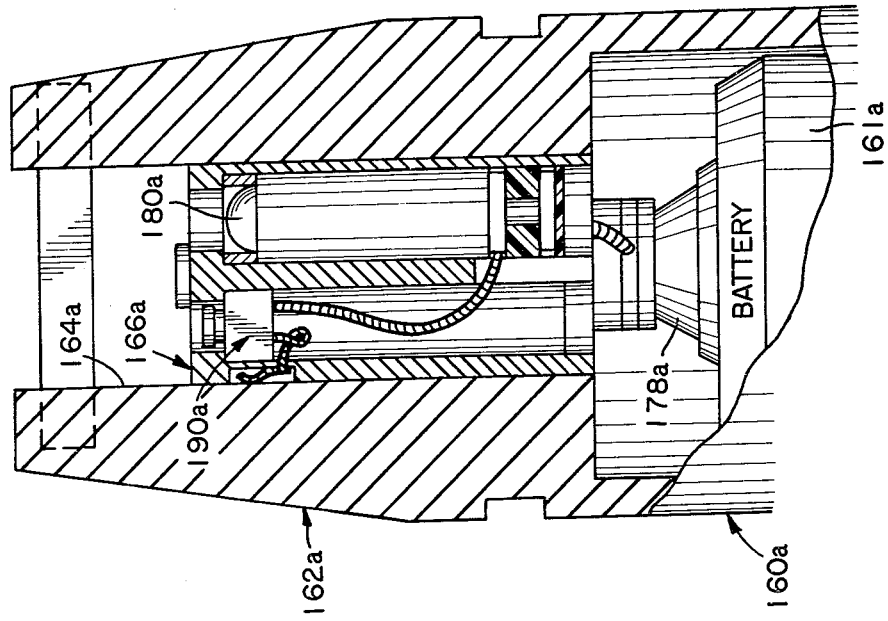
FIG. 16 is a view similar to FIG. 13 but showing the bulb and a switch in a cartridge for mounting in laryngoscope handle.

FIGS. 16 and 17 are views showing a handle 160a which has an upper member 162a provided with a central, rectangular slot 164a for receiving a cartridge 166a containing a bulb 180a, a standard cartridge 172 of the type shown in FIGS. 33 and 34 in a space 170a, and a microswitch 190a. The cartridge is inserted into opening 164a until the cartridge makes electrical contact with the end terminal 178a of a battery 161a. The cartridge is held in place by a set screw 163a threaded into a side opening 165a in member 162a. The cartridge and handle are shown in elevation in FIG. 18.

Figure 19:
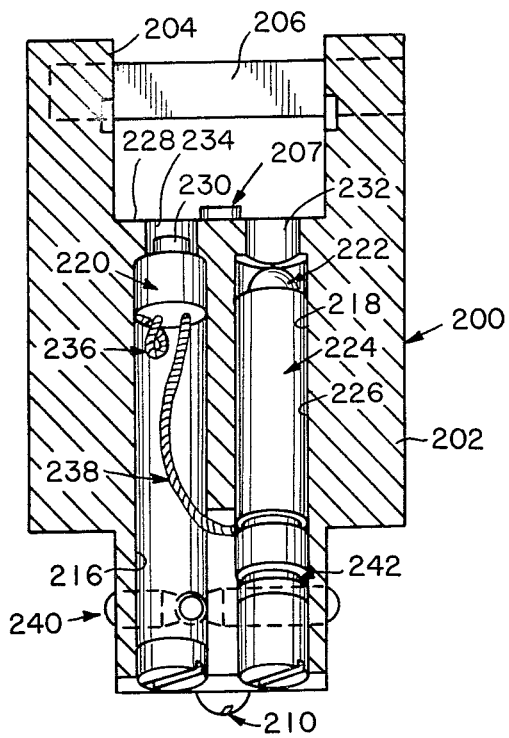
FIG. 19 is a cross-sectional view of a metallic adapter for mounting in a standard laryngoscope handle.
Figure 20:
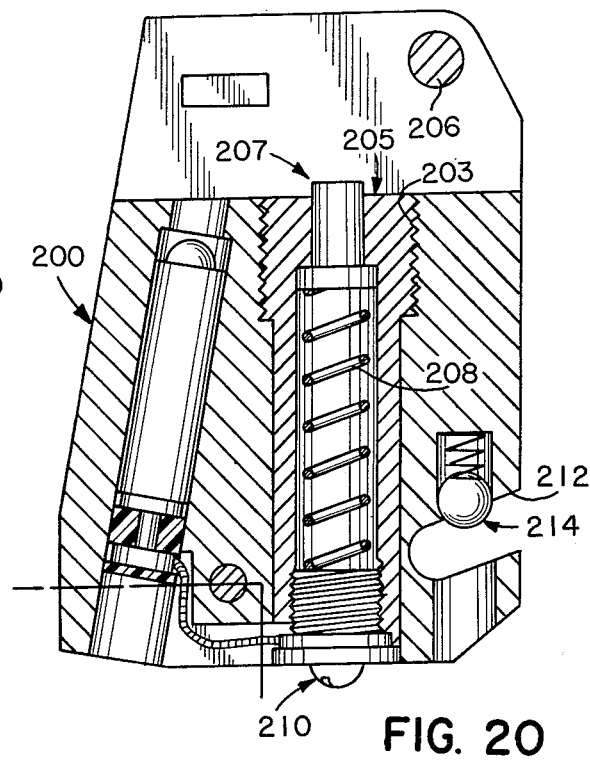
FIG. 20 is a second cross-sectional view of the adapter in FIG. 19.

FIGS. 19 and 20 show several views of a metallic adapter for use on a handle with a conventional or non-conventional laryngoscope blade. The adapter, denoted by the numeral 200, includes a metallic member 202 having the usual slot 204 provided with a crossbar 206 for attachment to the base of a blade having a slot, such as slot 104 of base 100 (FIG. 9). Member 202 has a central passage 203 for receiving a conventional cartridge 205 of the type having an electrical contact 207 coupled through a metallic, coil spring 208 to an end contact 210 for connection to a battery contact in the conventional handle with which adapter 200 is to be used. Adapter 200 has a side slot 212 and a ball detent 214 to receive the conventional crossbar of a conventional laryngoscope handle in the usual manner.

Member 202 has two additional, side-by-side, generally parallel passages 216 and 218, passage 216 having a microswitch 220 near the upper end thereof and passage 218 having a light bulb 222 in a housing 224 surrounded by an insulating sleeve 226 inserted into passage 218. The light bulb is recessed inwardly from the upper end surface 228 of member 202. Similarly, the pushbutton actuater 230 of microswitch 220 is also recessed below surface 228. Thus, the recess 232 aligned with the light bulb is adapted to receive the end of the fiber optics bundle on the base of a non-conventional blade which is to be coupled to the upper end of adapter 200. Similarly, the recess 234 aligned with the microswitch is adapted to receive a projection on the non-conventional blade base for actuating the microswitch, which through wires 236 and 238, connects light bulb with the battery in the handle with which adapter 200 is associated. In this way, a light will travel from the light bulb through the fiber optics bundle to the outer end of the blade for illuminating the throat of the patient as the blade is inserted into the throat. If a conventional blade is used with adapter 200, light bulb 222 is not actuated and cartridge 205 will connect the light bulb on the conventional blade with the standard cartridge and battery of the handle.

Figure 22:
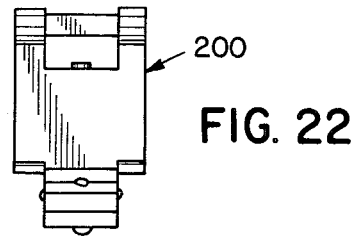
FIGS. 22, 23 and 24 are different elevational views of the adapter.
Figure 25:
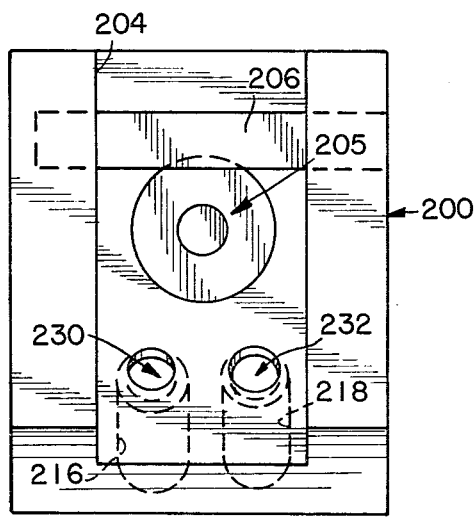
FIG. 25 is a top plan view of the adapter.
Figure 24:
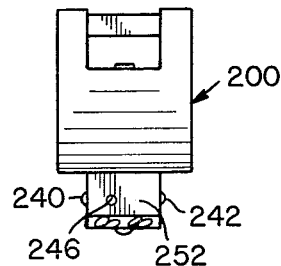
Figure 23:
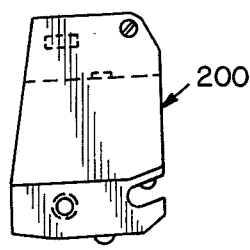
Figure 26:
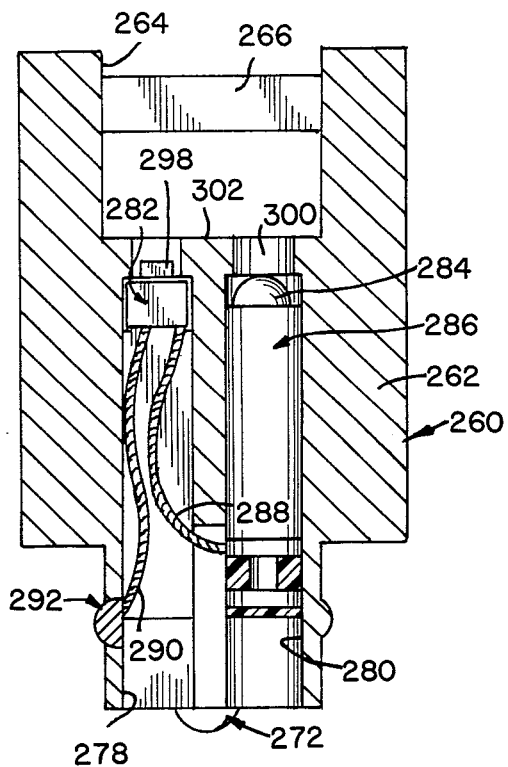
FIGS. 26 and 27 are views similar to FIGS. 19 and 20 but showing a plastic adapter.
Figure 27:
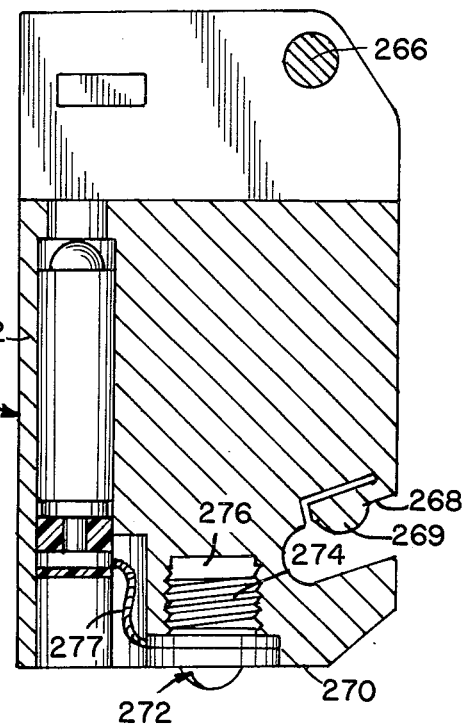

FIGS. 22, 23 and 24 show elevational views of adapter 200. FIG. 25 shows a top plan view of the adapter.

Figure 21:
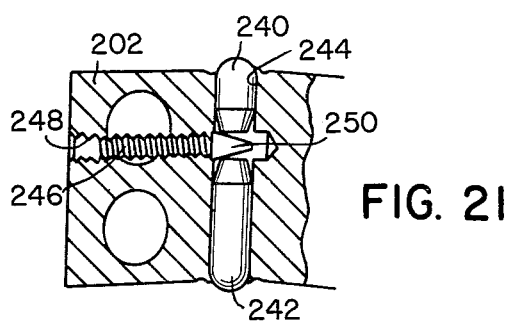
FIG. 21 is an enlarged cross-sectional view of the locking mechanism for holding the adapter of FIGS. 19 and 20 in place on a handle.

The adapter is held in place by a structure shown in FIG. 21. To this end, a pair of wedges 240 and 242 are mounted in a passage 244 in body 202 as shown in FIGS. 19, 20 and 21. A set screw 246 is threaded into a passage 248 perpendicular to passage 244 and has a conical end face 250 which bears against the adjacent ends of wedges 240 and 242 to force the wedges outwardly and against the adjacent surfaces of the conventional handle with which adapter is associated. FIG. 24 also shows screw 246 and the way in which wedges 240 and 242 project laterally from a base portion 252 of adapter 200.

Passages 216 and 218 of adapter 200 are located at an angle so that they can be carried by adapter 200 without interference with cartridge 205. If they were parallel with the cartridge, there would not be sufficient structure to allow for the presence of the light bulb and the microswitch without weakening the overall structure of the adapter.

Figure 28:
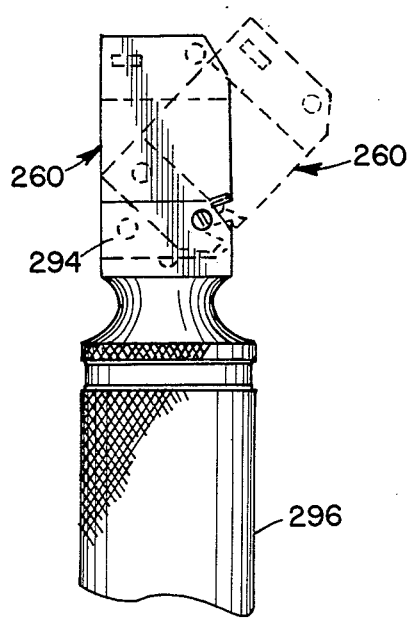
FIG. 28 is a side elevational view of either adapter on a conventional handle.
Figure 29:
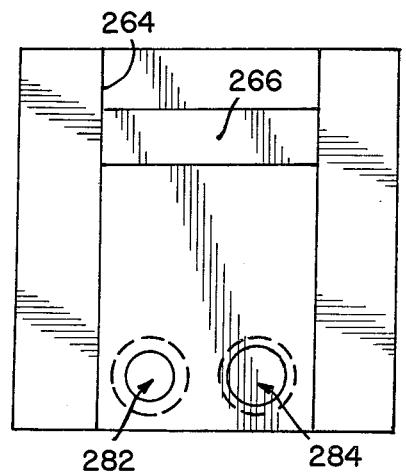
FIG. 29 is a top plan view of the adapter of FIGS. 26 and 27.

FIGS. 26-29 show another form of an adapter which is made of plastic rather than metal as in the case of adapter 200. Adapter 260 has a plastic body 262 provided with an upper slot 264 an a crossbar 266 for attachment to the base of a non-conventional laryngoscope blade. Body 262 also has a slot 268, a detent 269, and a bottom surface 270 provided with an electrical contact 272 for attachment in the usual fashion with the upper end of a conventional laryngoscope handle. This is shown in FIG. 28, the adapter 260 being shown in an operative position in full lines and in a position ready to be removed from the handle in dashed lines.

Contact 272 has a threaded upper end 274 which is threaded into a passage 276 extending inwardly from surface 270 of body 262. A wire 277 makes electrical contact between a light bulb 284 and contact 272. The adapter has a pair of side-by-side, generally parallel passages 278 and 280 for receiving, respectively, a microswitch 282 and light bulb 284, the latter being carried in a housing 286 and coupled by wire 288 to microswitch 282. A second wire 290 from the microswitch extends to a metal contact 292 for making electrical contact with the adjacent metallic part 294 of conventional handle 296 (FIG. 28). Thus, when adapter 260 is placed on handle 296 in the manner shown in FIG. 28, bulb 284 will be ready to be energized because contact 272 will be coupled to the central terminal of the battery in handle 296 and contact 292 will make electrical contact with part 294 (FIG. 28). When switch 282 is closed, i.e., when the pushbutton actuator 298 of the switch is pressed downwardly by a projection on a non-conventional blade base coupled with the upper end of the adapter, the light will come on and will pass through a fiber optics bundle whose end is inserted in the recessed opening 300 of passage 280 adjacent to surface 302 of the adapter body 262. Adapter 260 shows that the light source 284 can be accommodated without enlarging the adapter body as in the case of the adapter shown in FIGS. 19 and 20.

Figure 14:
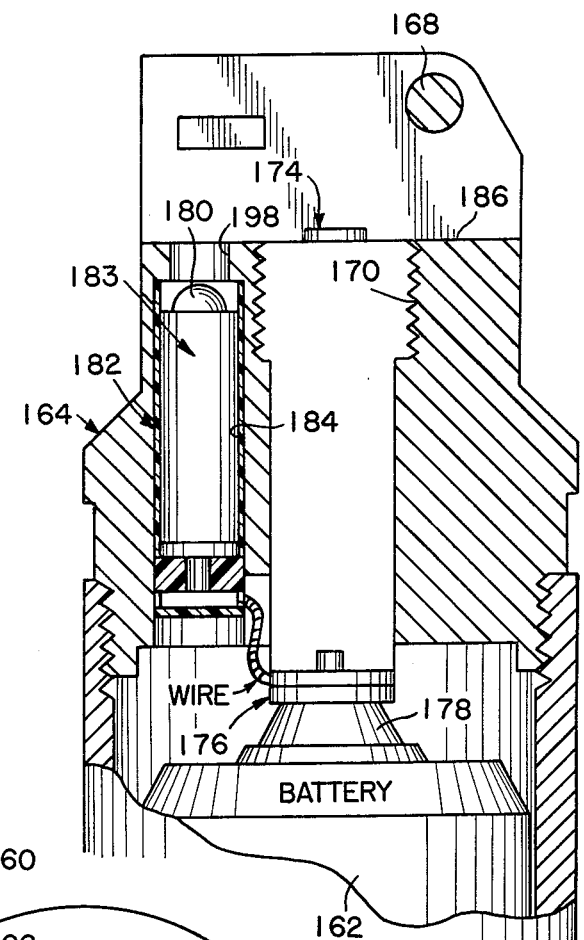
FIG. 14 is a view of the handle of FIG. 13 but rotated through an angle of 90°.

FIG. 30 is a view of a non-conventional laryngoscope blade 310 having a base 312 provided with a projection 314 and a fiber optics bundle 316 having an end 318. Projection 314 and 318 are shown inserted into the end recesses of a pair of passages 320 and 322 containing respectively a microswitch 324 and a light bulb 326. Thus, projection 314 is shown as actuating the microswitch 324 while the fiber optics end 318 is shown aligned optically with the light bulb 326 to receive light therefrom. FIG. 30 illustrates how a base of a blade is used to actuate the light source of adapter 200 of FIGS. 19 and 20 and adapter of 260 of FIGS. 26 and 27, also handle 160 of FIGS. 13 and 14 and handle 160a of FIGS. 16 and 17.

Figure 31:
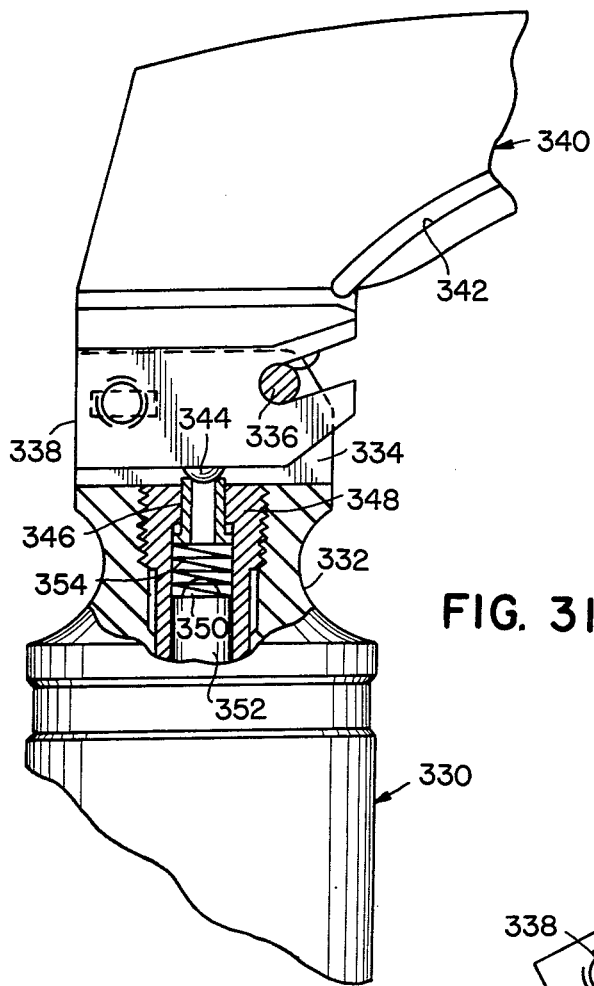
FIG. 31 is a view similar to FIG. 30 but showing a light bulb mounted in a central cartridge in the handle.
Figure 32:
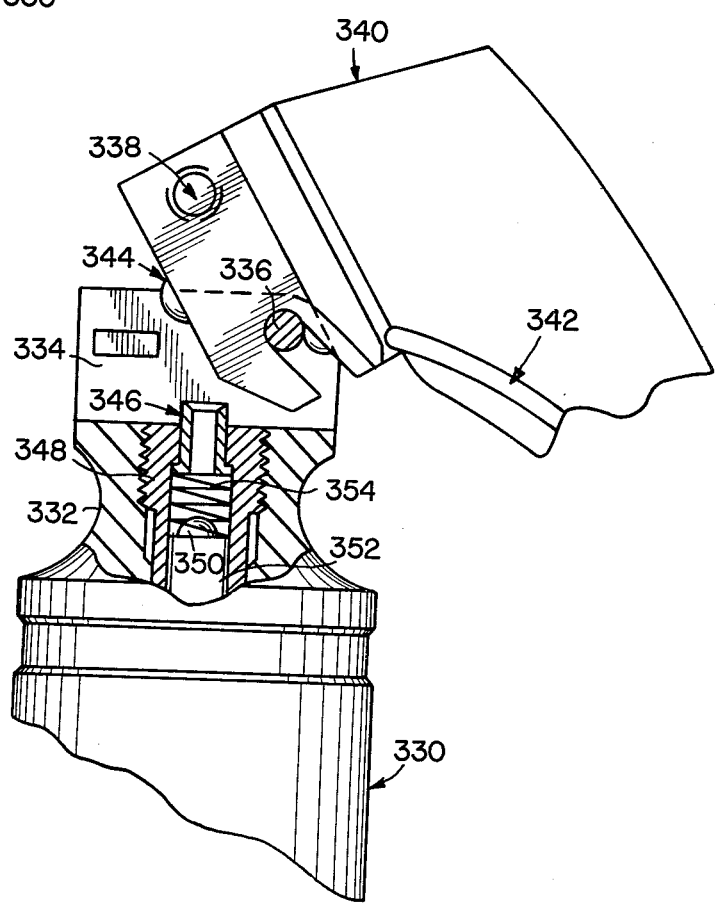
FIG. 32 is a view similar to FIG. 31 but showing the blade pivoted out of position, disabling the light bulb in the cartridge.

Another type of handle for a conventional or non-conventional blade is denoted by the numeral 330 and is shown in FIGS. 31 and 32. Handle 330 has an upper end 332 provided with a slotted part 334 and a crossbar 336 for receiving the base 338 of a conventional blade 340. The blade has a wiring channel 342 which extends to the outer end of the blade for connection to a light blade but has one end which is electrically coupled to a metallic projection 344 projecting outwardly from the end face of base 338.

End 332 has a cartridge 348 threadably coupled thereto, the cartridge containing a light bulb 350 in a housing 352 which makes electrical contact with a terminal of a battery (not shown) carried by handle 330. The body of cartridge 348 is of insulating material so that it will not interfere with the electrical connection made to the battery by housing (e.g. bulb jacket) 352. A coil spring 354 is in the space above the light bulb and makes electrical contact with projection 344 through a tubular metallic sleeve 346 slidable in the upper end of the passage which contains light bulb 350. Before blade base 338 is snapped into place as shown in FIG. 32, sleeve 346 projects outwardly and does not make electrical contact with metallic projection 344. When the base is in place as shown in FIG. 31, sleeve 346 places housing 350 in electrical contact with metallic projection 344 through spring 354. Thus, voltage from the battery will be applied through the cartridge, through the tubular sleeve 346, and through the wiring in channel 342 to the light bulb at the outer end of the blade. Light bulb 350 will be actuated in this case.

FIG. 35 shows a non-conventional blade 360 with handle 330. Blade base 374 has a fiber optics bundle 376 having one end 378 alignable with sleeve 346 when the blade base 374 is in place as shown in FIG. 35. When this occurs, a conductive metal tape 380 on the bottom surfaces of blade base 374 makes electrical contact between sleeve 346 and the crossbar 336 of handle 330. In this way, an electrical circuit between the light bulb 350 and the battery in handle 330 is completed to turn the light bulb on and cause light to travel upwardly through sleeve 346 and into and through the fiber optics light guide 376 to the outer end of the blade. FIGS. 36 and 37 show different views of the blade base. These views also show the position of metallic strip or tape 380 with respect to the adjacent end 378 of the fiber optics bundle 376.

Figure 39:
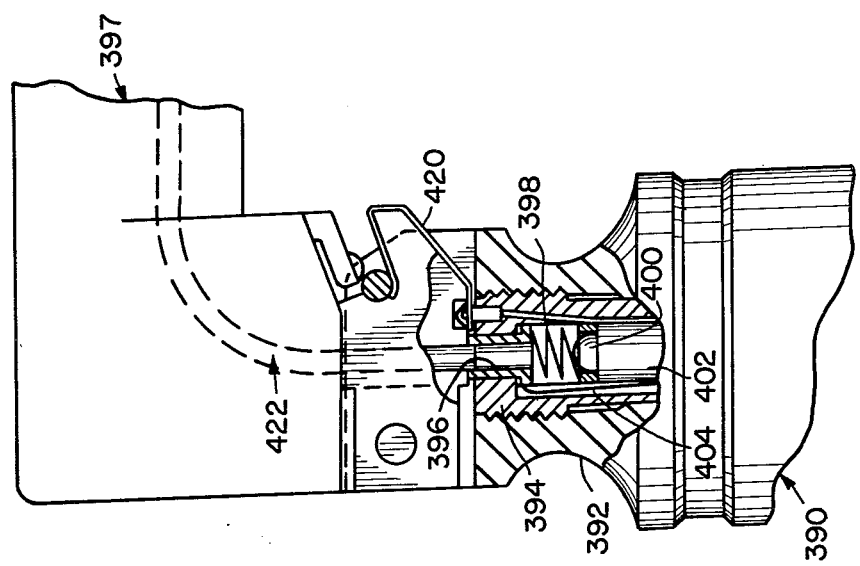
FIG. 39 is a view similar to FIG. 38 but showing the central cartridge of FIG. 38 with a non-conventional blade.
Figure 38:
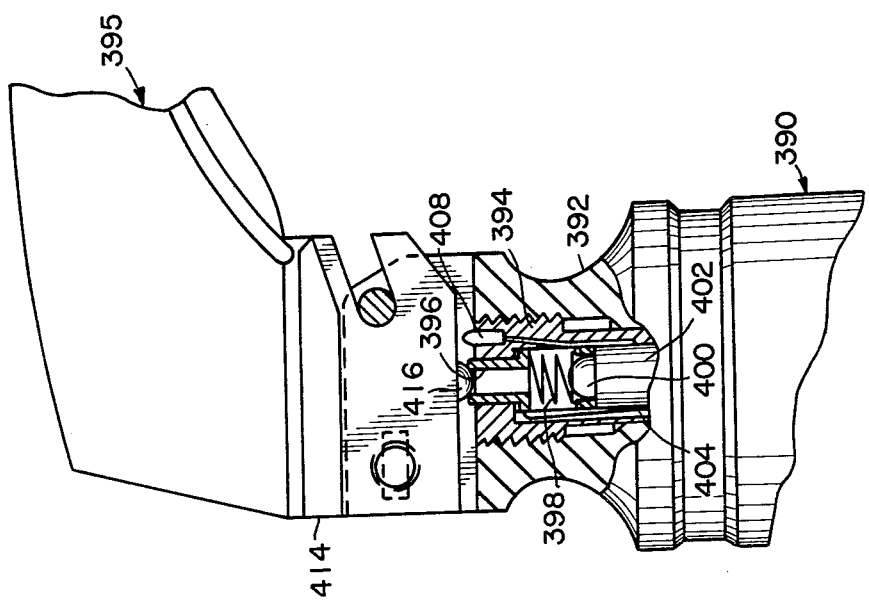
FIG. 38 is another type of central cartridge in a handle for use with a conventional blade.

FIGS. 38 and 39 show a handle 390 having an upper end 392 provided with a different embodiment of a cartridge 394 for use either with a conventional blade 395 (FIG. 38) or with a non-conventional blade 397 (FIG. 39). The cartridge has an upper tubular sleeve 396, coil spring 398, a light bulb 400 and a bulb jacket 402 and a first wire 404 connected metallic sleeve 396 with one part of the battery in handle 390 when a conventional blade is used. A second wire 406 having an upper contact 408 is electrically connected to housing 402 whereby the other part of the battery in the handle can be connected to the bulb when a non-conventional blade is used.

Blade 395 has a base 414 provided with a metallic projection 416 which makes electrical contact with sleeve 396 when the blade is in place as shown in FIG. 38. This causes the light bulb at the outer end of the blade to be energized by the electrical circuit comprised of the metal of the handle itself and wire 404.

Figure 42:
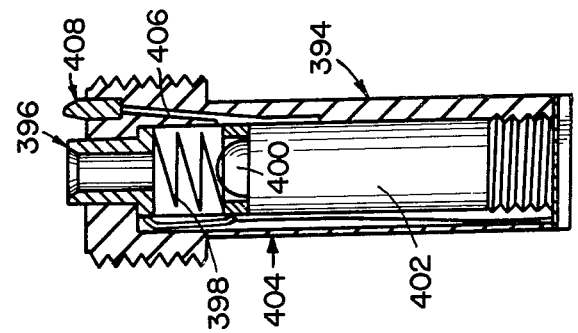
FIG. 42 is a cross-sectional view of the cartridge of FIG. 38.

In the case of non-conventional blade 397, the base of the blade has a metallic conductive strip or tape 420 which makes electrical contact with contact tip 408 in a manner shown in FIG. 39 to actuage light bulb 400. A fiber optics light bundle 422 extends into sleeve 396, so that when the light bulb 400 is energized, light will enter the fiber optics light bundle and be passed outwardly to the outer end of the blade 397. FIG. 42 shows the cartridge 394 in greater detail.

Figure 43:
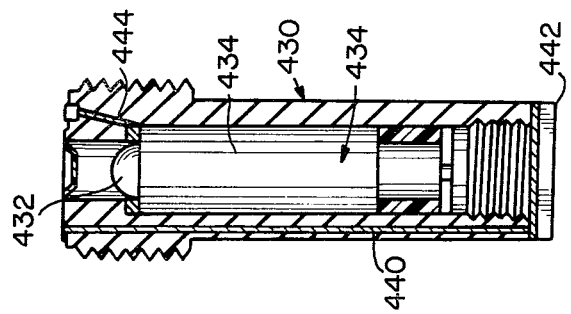
FIG. 43 is a cross-sectional view of the cartridge of FIG. 40.
Figure 44:
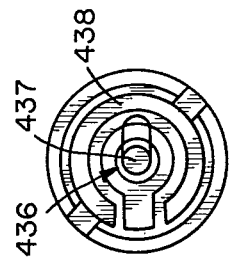
FIG. 44 is a top plan view of the cartridge of FIG. 43.

FIG. 43 shows a different embodiment of the cartridge denoted by the numeral 430 for use with handle 390. It includes a light bulb 432 in a housing 434 having a first upper electrical contact 436 surrounded by a second electrical contact 438 as shown in FIG. 44. A center hole 437 is in contact 436. A wire 440 makes electrical connection between contact 436 and a bottom contact 442 which engages the battery central terminal in the handle with which cartridge 430 is used. A second wire 444 makes electrical connection with contact 438 and is also connected to housing 434.

Figure 40:
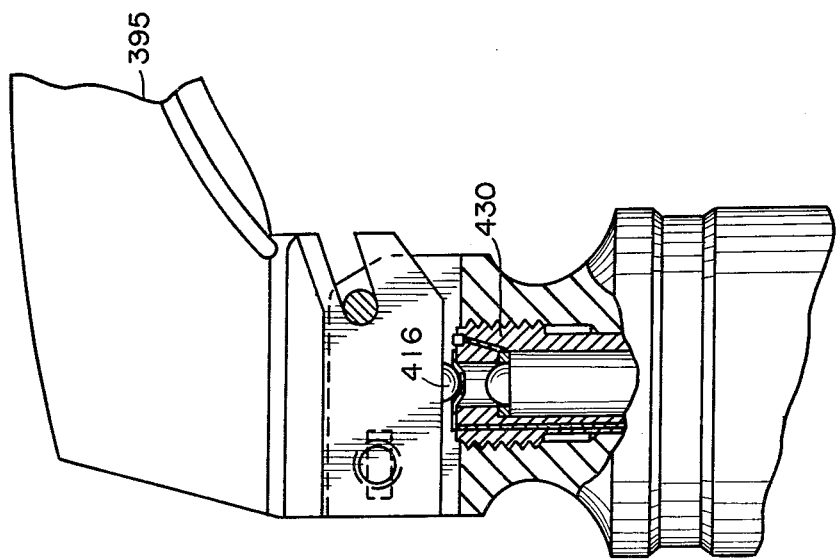

Cartridge 430 in handle 390 can be used with conventional blade 395 in the manner shown in FIG. 40. In this case, contact 416 engages contact 436 to connect to the battery through wire 440 while contact 438 is not used. When blade is in the operating position of FIG. 40, light bulb 432 is not energized but battery voltage is applied to the light bulb at the outer end of the blade 395.

Figure 41:
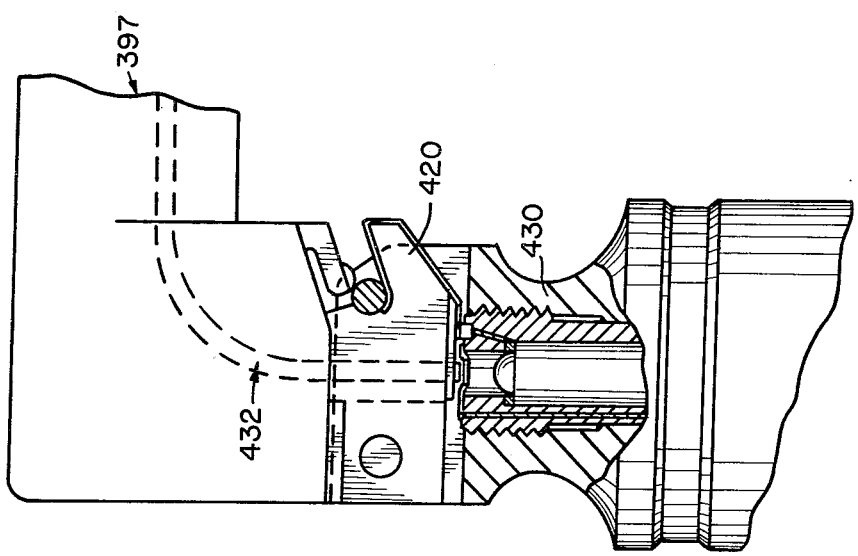
FIGS. 40 and 41 are views similar to FIGS. 38 and 39 but show additional embodiments of a central cartridge with conventional and non-conventional blades.

When cartridge 430 is used with non-conventional blade 397, contact 438 makes electrical connection with tape 420 as shown in FIG. 41 and this causes bulb 432 to be actuated to in turn cause light to pass through central hole 437 (FIG. 44) in contact 436 and then into the fiber optics bundle 432. The light then travels to the outer end of the fiber optics bundle at the outer end of blade 397.

Figure 45:
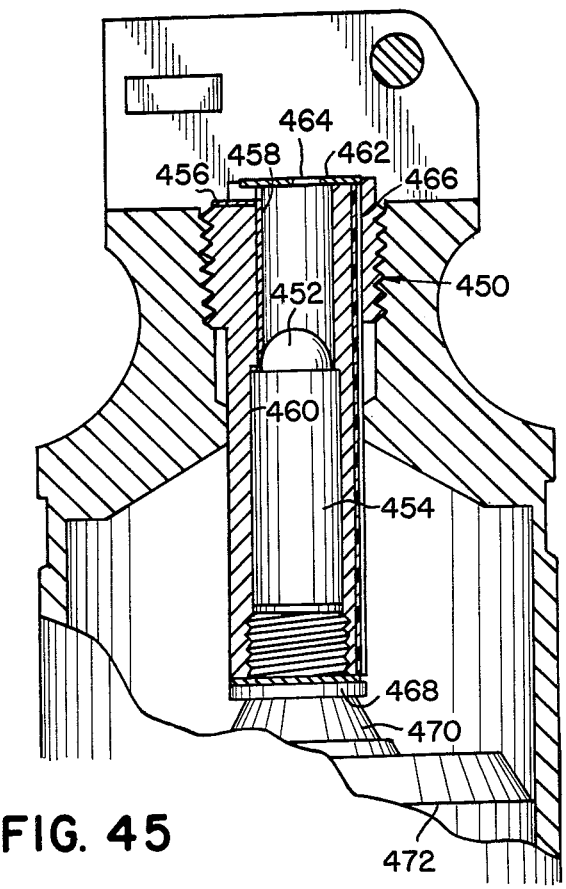
FIG. 45 is a view of another central cartridge for use with conventional and non-conventional blades.
Figure 46:
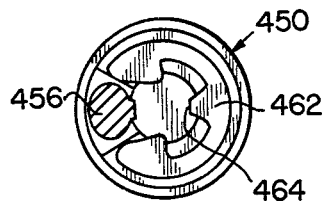
FIG. 46 is a top plan view of the cartridge of the handle of FIG. 45.

FIG. 45 shows another embodiment of a cartridge 450 for use either with a conventional blade or a non-conventional blade similar to blades 395 and 397 of FIGS. 38-41. Cartridge 450 is mounted in a handle 390 and has a light bulb 452 in a housing 454. A first metallic element 456 near the upper end of the cartridge has a lead or wire 458 coupled to housing 454 at location 460. A second metallic member 462 has a central recess 464 therein. Contact 462 makes electrical contact by a wire 466 to the bottom contact 468 on the cartridge which makes electrical contact with the central contact 470 of a battery 472 in the handle 390 with which the cartridge is used.

When a conventional blade is used, the metallic projection of the blade, such as projection 416 on blade 397 of FIG. 38, will make electrical contact with contact 462 which, through wire 466 and end contact 468 will make electrical connection with battery terminal 470 and in bypassing relationship to light bulb 452. Thus, the light bulb 452 will not be energized but voltage will be applied to the light bulb on the outer end of the conventional blade connected to the handle 390.

Figure 47:
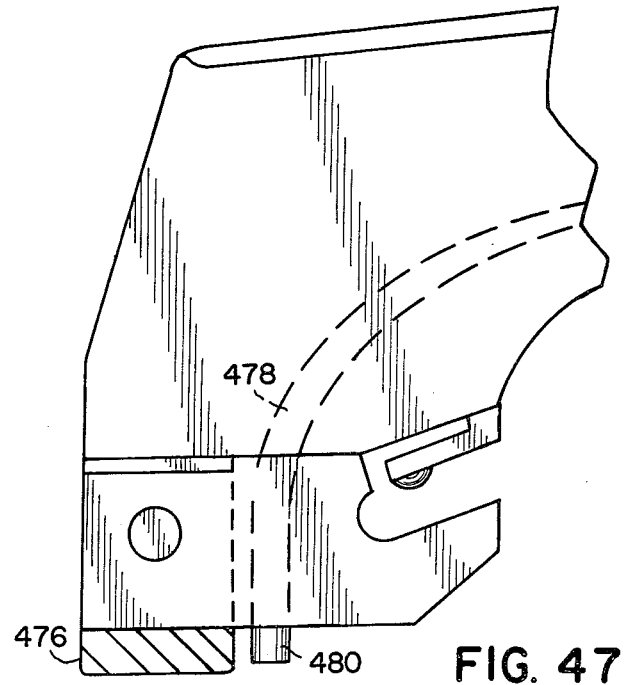
FIG. 47 is a fragmentary side elevational view of the base of a non-conventional blade for use with the cartridge of FIG. 45.

When a non-conventional blade of the type shown in FIG. 47 is used, the blade will have a deformable metallic projection 476 which will engage element 456, causing bulb 452 to be energized to cause light to travel upwardly and through a fiber optics light bundle 478 whose lower end 480 will extend into recess 464 optically aligned with bulb 452.

FIGS. 48-50 show another type of handle 500 which can be used either with a conventional or non-conventional laryngoscope blade. In this embodiment, handle 500 has an upper member 502 threadably mounted on the handle body as shown in FIGS. 48 and 49. Member 502 has a conventional cartridge 504 of the type shown in FIGS. 33 and 34 for use with a conventional blade having a light source on the outer end of the blade. When the blade base is coupled in the usual fashion to slot 506 and with the crossbar 508 of member 502, voltage is supplied from battery 510 in handle 500 through the blade base and the wiring channel to the light bulb is at the outer end of the blade.

Figure 51:
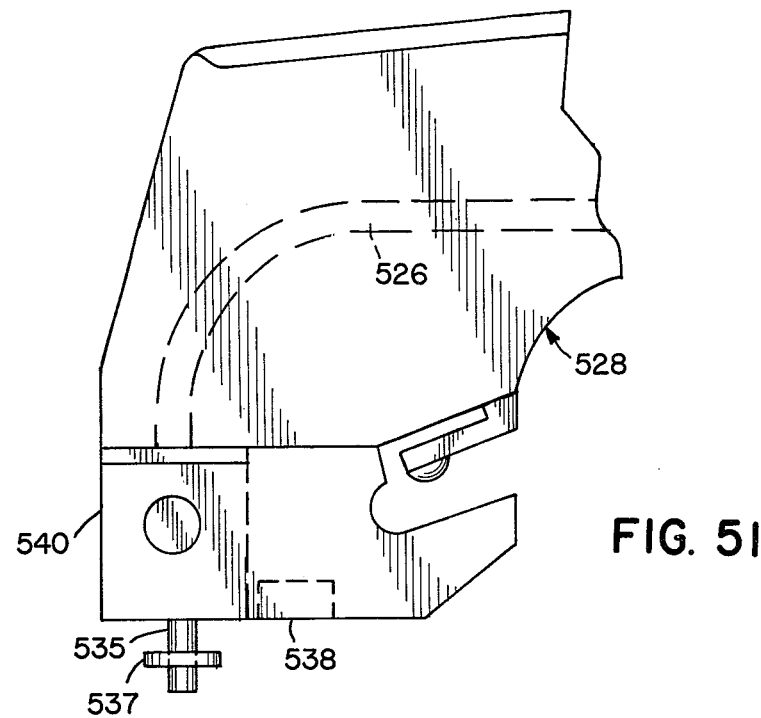
FIGS. 51 and 52 are side and bottom views, respectively, of the base of the non-conventional blade for use with the handle of FIG. 48.
Figure 52:
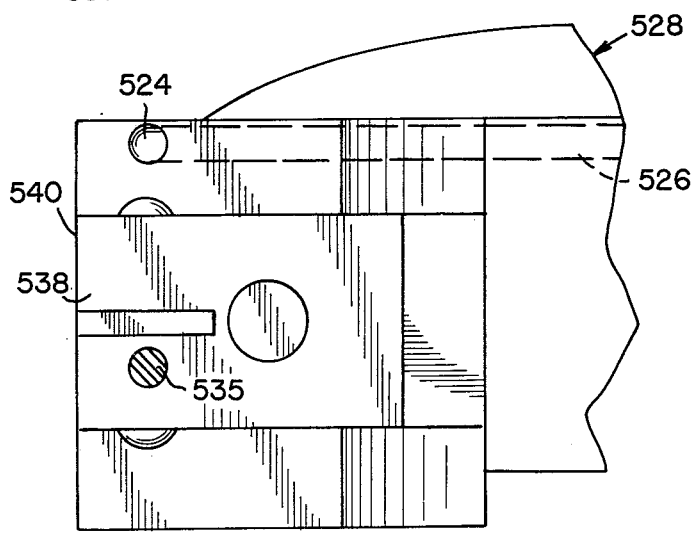

For use with a non-conventional blade, member 502 has a passage 512 near one side 514 thereof for receiving a light bulb 516 in a housing 518 surrounded by an insulating sleeve 520. Bulb 516 is recessed to present an opening 522 for receiving one end 524 (FIG. 52) of a fiber optics light bundle 526 of a non-conventional blade 528 (FIGS. 51 and 52).

A second cartridge 530 similar in all respect to cartridge 504 is in a passage which is offset from the center line of member 502 as shown in FIG. 50. Cartridge 530 has a member 532 which is shiftable in a passage 534 but which can be engaged by a metallic shaft 535 (FIG. 51) carried by a non-conventional laryngoscope blade. Shaft 535 has a flexible metallic washer 537 which makes electrical contact with handle 502 as shown in dashed lines to cause light bulb 516 to be supplied with voltage through wires 517 and 519 from battery 510 when shaft 535 on the bottom of face 538 of blade base 540 of blade 528 extends into recess 534. Thus, light from light bulb 516 will enter end face 524 of the fiber optics light guide 526 and will travel to the outer end of blade 528. In this way handle 500 can accommodate a conventional blade and a non-conventional disposable blade.

Figures 52A, 53:
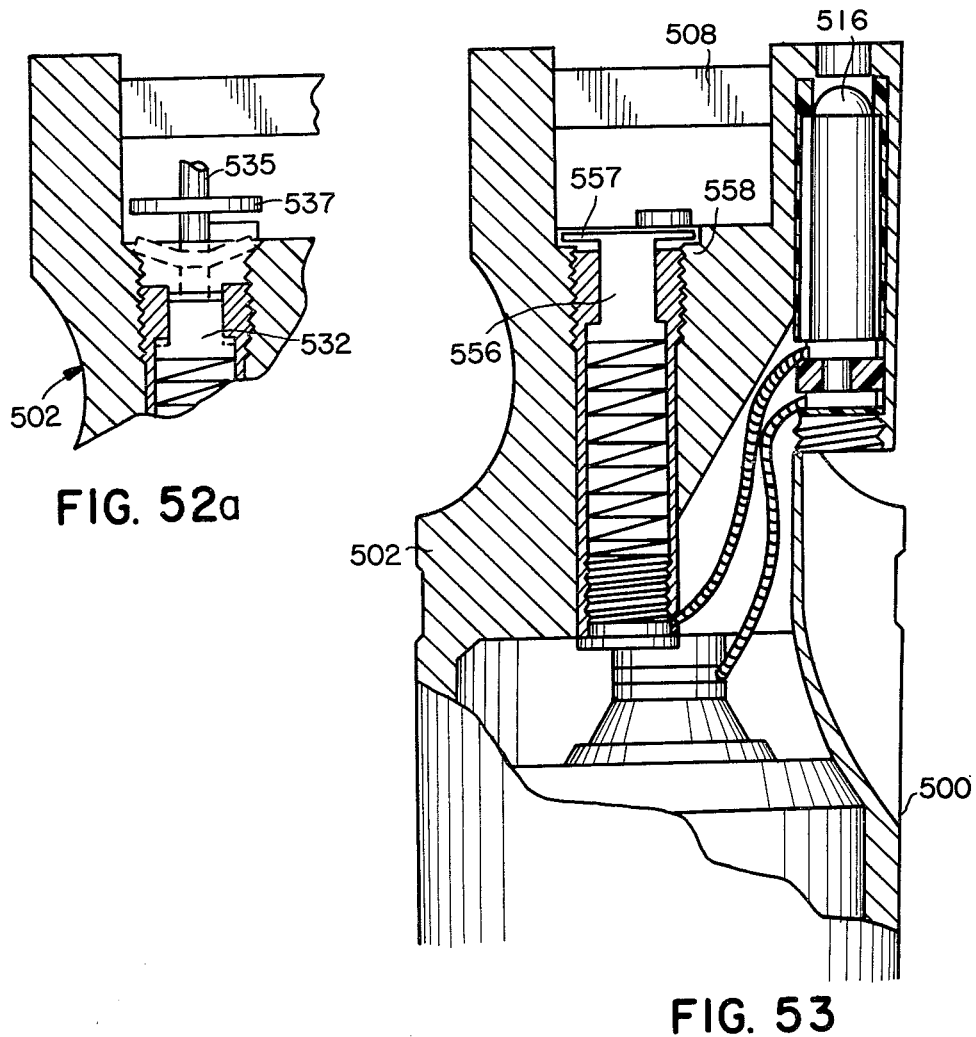
FIG. 52A is a fragmentary view of the handle of FIG. 48 showing how the light bulb is energized.
FIG. 53 is a view similar to FIG. 48 but showing another cartridge in the handle; and, FIG. 54 is a view showing slight modification of the handle of FIG. 53.
Figure 54:
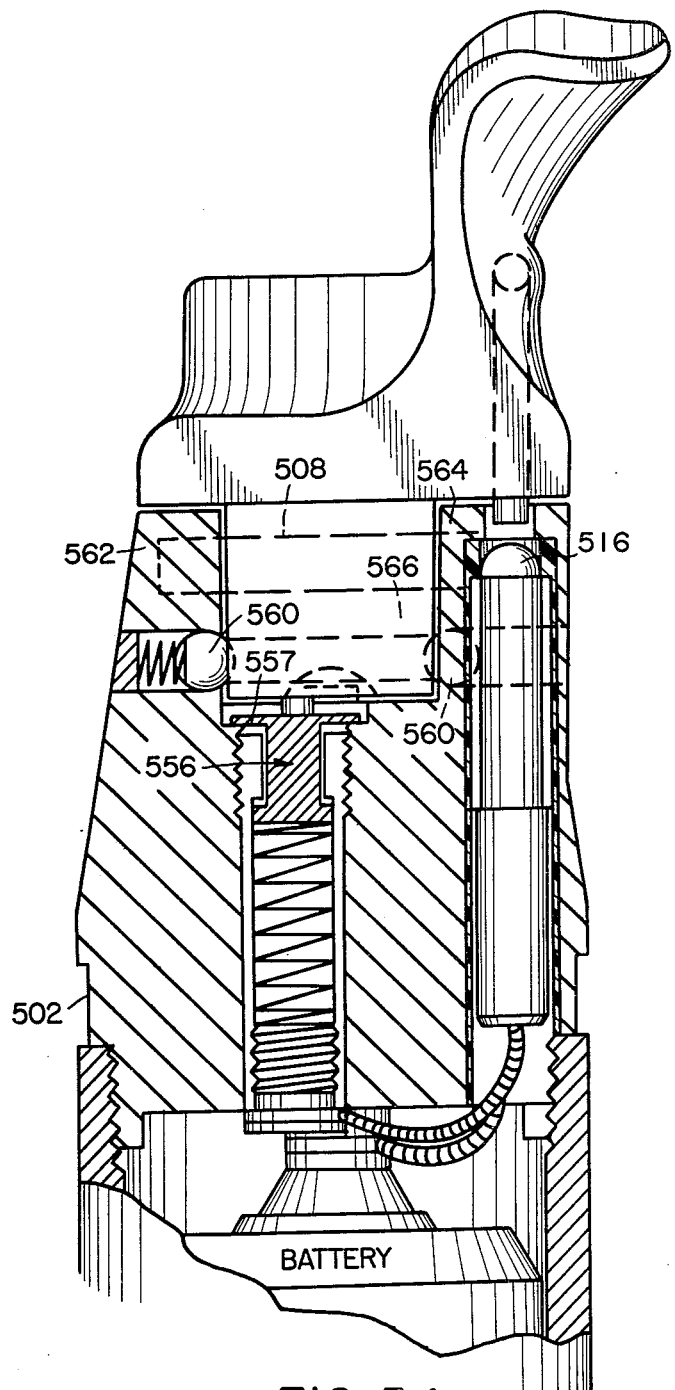

FIGS. 53 and 54 show modifications of the cartridge of FIGS. 48-50 wherein the cartridge has a reciprocal member 556 with a flat top part 557 which is forced downwardly by projection on a non-conventional blade to make electrical contact with the base of the blade and the adjacent part 558 of the handle. FIG. 54 shows spring biased ball detents 560 carried by the handle parts 562 and 564 for entering recesses in the opposite sides of blade base 566 to releasably hold the base to the handle.

I claim:

1. A laryngoscope having a handle including an electrical power source, a blade having a forwardmost end and a rearwardmost end, the latter defining a mounting base; and means forming part of said handle and part of said mounting base for disengagably connecting said base with said handle, the improvement comprising: a light source carried by said handle; a light guide carried by said blade and extending from its base to its forwardmost end; and a cooperating arrangement forming part of said handle and part of said base for causing said power source to energize said light source when said blade is disengagably connected with said handle, said cooperating arrangement including a passage in said handle, electrical connection means for coupling said light source with said power source, said electrical connection means being disposed within said passage so as not to extend outwardly of said passage, said arrangement also including a projecting member carried by the base of said blade for engaging said electrical connection means when said blade is disengagably connected with said handle in order to cause said power source to energize said light source, said blade including said projection being one type of laryngoscope blade and said handle including an arrangement separate from said last-mentioned arrangement for cooperating with a second, different type of blade which carries its own light source such that said second blade is disengagably connectable with said handle such that said second arrangement causes the power source in said handle to actuate the light source carried by said second blade while not causing said power source to actuate the light source carried by said handle.

2. A laryngoscope having a handle including an uppermost blade connecting end portion, a blade having a forwardmost end and a rearwardmost end, the latter defining a base; and an arrangement forming part of the base of said blade and the blade connecting portion of said handle for disengagably connecting said blade with said handle, the improvement comprising an adapter serving as said blade connecting portion of the handle and a connecting arrangement forming part of said adapter and part of the rest of said handle for disengagably connecting said adapter with the rest of said handle, said connecting arrangement including a pair of upstanding walls including confronting spaced-apart surfaces forming part of the rest of said handle, a pair of aligned, relatively shiftable projections carried by said adapter, and means shiftably carried by said adapter for moving the projections apart and against said confronting surfaces of said upstanding walls in order to releasably secure said adapter to the rest of said handle.

3. A laryngoscope having a handle including an electrical power source, a blade having a forwardmost end and a rearwardmost end, the latter defining a mounting base, and means forming part of said handle and part of said mounting base for disengagably connecting said base with said handle, the improvement comprising: a light source carried by said handle; a light guide carried by said blade and extending from its base to its forwardmost end; and a cooperating arrangement forming part of said handle and part of said base for causing said power source to energize said light source when said blade is disengagably connected with said handle, said arrangement including a passage into said handle from one surface thereof and electrical connection means disposed within said passage in a recessed manner inward of said handle surface, said arrangement also including means carried by and projecting from the base of said blade for entering said passage from said handle surface so as to engage said electrical connection means when said blade is disengagably connected with said handle in order to cause said power source to energize said light source.

4. The improvement according to claim 3 wherein said electrical connection means includes contact means for engagement with said projection.

5. The improvement according to claim 3 wherein said electrical connection means includes a switch having a movable actuator for engagement with said projection.

6. The improvement according to claim 3 wherein said laryngoscope includes a second alternate blade having its own light source and mounting base and means forming part of said handle and part of the base of said alternate blade for disengagably connecting the base of said alternate blade with said handle while, at the same time, causing said power source to energize the alternate blade's light source without contacting said electrical connection means whereby the light source carried by said handle is not energized by said alternate blade.

7. The improvement according to claim 6 wherein said means for causing said power source to energize the blade's light source includes means projecting outward from said handle and wherein said first-mentioned blade includes an opening for preventing that blade from engaging said last-mentioned projecting means when the first-mentioned blade is disengagably connected with the handle.

8. A laryngoscope comprising: a handle including a light source, power source means and an uppermost blade connecting end having first and second electrically isolated contact means, each of which is electrically connected to said power source means; a first blade having means including a light source thereon and means for mounting the first blade with the blade connecting end of said handle in a way which engages said first contact means without engaging said second contact means for causing said power source means to energize its light source; and a second blade carrying a light guide and having means for mounting the second blade with the blade connecting end of said handle in a way which engages said second contact means without engaging said first contact means for causing said power source means to energize the light source carried by said handle while placing said light guide in optical communication with said last-mentioned light source.

9. In a laryngoscope having a first blade provided with a base: a handle having means thereof for releasably connecting the base of the blade in an operative position thereon, said handle having means for mounting an electrical power source thereon; a light source carried by the handle near said connecting means; and means coupled with said light source and responsive to the placement of said base in said operative position for actuating the light source, whereby light from the light source can enter and travel through a fiber optics light guide carried by the blade, said handle having an upper end provided with a pair of first and second cartridge therein, the first one of the cartridges being provided for a second laryngoscope blade having a light source at the outer end of the blade, said first cartridge having means including an outward projection electrically coupling the second blade's light source with the power source carried by the handle when the second blade is removably coupled to the handle in engaging relationship with said outward projection, the second cartridge being provided for a first laryngoscope blade and having contact means in electrical connection with said power source, there being a passage adjacent to the cartridges and a light source in the passage, the first blade having a fiber optics light guide optically aligned with the light source, a projection engaging the contact means of the second cartridge when the first blade is removably coupled with the handle and an opening for preventing said first blade from engaging the outward projection of said first cartridge, the second cartridge electrically connecting the light source with said power source when the projection on said first blade engages said contact means.

10. A laryngoscope comprising:
a handle including a gripping portion containing power source means and a head portion including means for disengagably receiving a laryngoscope blade having its own light source, said head portion including means for electrically connecting said light source to said power source means when said blade is disengagably received by said head portion whereby to energize said light source; an adapter including its own light source and means for disengagably receiving a laryngoscope blade which does not include a light source but rather a light guide such that one end of said light guide is automatically placed in optical alignment with the adapter's light source when said last-mentioned blade is disengagably received by said adapter; and means forming part of said adapter and part of said laryngoscope handle for electrically connecting the light source carried by said adapter in circuit with said power source means when and only when said second-mentioned laryngoscope blade is disengagably received by said adapter and said adapter is disengagably received by said handle, whereby to energize the light source carried by said adapter and cause light therefrom to pass through said light guide.

11. A laryngoscope according to claim 10 wherein said means forming part of said handle and said adapter includes means engaging said second-mentioned laryngoscope blade when the latter is disengagably received by said adapter for closing an electrical circuit between the light source carried by said receiver and said power source means, said means engaging said second-mentioned laryngoscope blade maintaining an open circuit between the light source carried by said adapter and said power source means when not engaged by said last-mentioned blade.

12. A laryngoscope according to claim 11 wherein said blade engaging means includes an electrical switch movable between the first position when engaged by said second-mentioned blade and a second position when not engaged by said blade.

13. A laryngoscope according to claim 10 wherein said adapter includes means for connecting it to the head portion of said handle, said connecting means including a pair of aligned, relatively shiftable projections carried by said adapter and means shiftably carried by said adapter for moving the projections apart whereby to engage against confronting surfaces forming part of the handle's head portion.

* * * * *